(12) United States Patent
Lazarev et al.

(10) Patent No.: US 8,246,612 B2
(45) Date of Patent: Aug. 21, 2012

(54) SCANNING LASER SYSTEM FOR THE TREATMENT OF TISSUE

(75) Inventors: Victor Lazarev, Billerica, MA (US); Doug Ely, North Andover, MA (US); Daniel Roth, Newton, MA (US)

(73) Assignee: Shaser, Inc., Lexington, MA (US)

( * ) Notice: Subject to any disclaimer, the term of this patent is extended or adjusted under 35 U.S.C. 154(b) by 830 days.

(21) Appl. No.: 12/375,862

(22) PCT Filed: Sep. 5, 2007

(86) PCT No.: PCT/US2007/019332
§ 371 (c)(1),
(2), (4) Date: Jan. 30, 2009

(87) PCT Pub. No.: WO2008/057154
PCT Pub. Date: May 15, 2008

(65) Prior Publication Data
US 2009/0326523 A1    Dec. 31, 2009

Related U.S. Application Data

(60) Provisional application No. 60/842,681, filed on Sep. 6, 2006.

(51) Int. Cl.
*A61B 18/20* (2006.01)
(52) U.S. Cl. ................... 606/9; 607/88; 607/90
(58) Field of Classification Search .......... 607/88–90; 606/9
See application file for complete search history.

(56) References Cited

U.S. PATENT DOCUMENTS

| | | | |
|---|---|---|---|
| 4,872,263 A | 10/1989 | Etheredge, III | |
| 5,005,287 A | 4/1991 | Ritter | |
| 5,336,217 A | 8/1994 | Buys et al. | 606/9 |
| 5,474,549 A | 12/1995 | Ortiz et al. | 606/9 |
| 5,968,033 A | 10/1999 | Fuller et al. | |
| 6,273,884 B1 | 8/2001 | Altshuler et al. | |
| 6,458,867 B1 | 10/2002 | Wang et al. | |
| 6,508,813 B1 | 1/2003 | Altshuler | |
| 6,770,069 B1 | 8/2004 | Hobart et al. | |
| 7,135,033 B2 | 11/2006 | Altshuler et al. | |
| 2002/0024547 A1* | 2/2002 | Miyakoshi | 347/14 |
| 2002/0035360 A1 | 3/2002 | Conners et al. | |
| 2003/0220632 A1 | 11/2003 | Strasser et al. | |
| 2005/0063199 A1 | 3/2005 | Levy et al. | |

(Continued)

FOREIGN PATENT DOCUMENTS
EP    0812547    12/1997
(Continued)

OTHER PUBLICATIONS
PCT International Search Report based on PCT/US2007/019332 dated Oct. 6, 2008.
(Continued)

*Primary Examiner* — Henry M Johnson, III
*Assistant Examiner* — Jeffrey Lipitz
(74) *Attorney, Agent, or Firm* — Guerin & Rodriguez, LLP

(57) ABSTRACT

The disclosed technology can be embodied within optical heads or other optical systems adapted for providing a selected dermatologic treatment (e.g., temporary hair growth management). This technology uses a scanner to mechanically change an orientation of an optical element, such as a light pipe, to facilitate the conveyance of light energy to multiple target/treatment locations on a patient's skin.

10 Claims, 31 Drawing Sheets

U.S. PATENT DOCUMENTS

| | | |
|---|---|---|
| 2005/0273089 A1 | 12/2005 | Kreindel et al. |
| 2006/0020309 A1* | 1/2006 | Altshuler et al. ............... 607/88 |
| 2006/0176912 A1* | 8/2006 | Anikitchev ....................... 372/9 |
| 2007/0219600 A1 | 9/2007 | Gertner et al. |
| 2009/0236495 A1* | 9/2009 | Jennings et al. ........... 250/201.2 |

FOREIGN PATENT DOCUMENTS

| | | |
|---|---|---|
| EP | 0960601 | 12/1999 |
| EP | 1118311 | 7/2001 |
| WO | WO2006/013567 | 2/2006 |

OTHER PUBLICATIONS

Office Action cited in U.S. Appl. No. 11/141,370 mailed May 18, 2010.

Office Action cited in U.S. Appl. No. 12/056,697 mailed Dec. 31, 2009.

Office Action cited in U.S. Appl. No. 12/056,697 mailed May 25, 2010.

* cited by examiner

DETECTOR IMAGE: INCOHERENT IRRADIANCE
LENS HAS NO TITLE.
SAT APR 1 2006
DETECTOR 12, NSCG SURFACE 1:
SIZE 10.000 W X 10.000 H MILLIMETERS, PIXELS 100 W X 100 H. TOTAL HITS = 49265
PEAK IRRADIANCE : 6.8550E+000 WATTS/CM^2
TOTAL POWER : 9.81016E-001 WATTS

SCANNING LASER SYSTEM FOR THE TREATMENT OF TISSUE

RELATED APPLICATIONS

This application is a national phase filing under 35 U.S.C. 371 of International Application No. PCT/US2007/019332, filed on Sep. 5, 2007, and claims the benefit of U.S. Provisional Application No. 60/842,681, filed Sep. 5, 2006, the entirety of these applications are hereby incorporated herein by reference for the teachings therein.

TECHNICAL FIELD

The disclosed technology relates generally to treating tissue and more specifically to dermatologic treatment using directed energy.

BACKGROUND

Light has been used in a wide range of medical applications for many years. In the field of dermatology high powered lasers and intense pulsed light (IPL) systems have been used to permanently remove unwanted hair, rejuvenate skin, remove veins etc. In the field of hair removal, devices remove hair from areas of the body with large diameter pulses of laser or incoherent light called intense pulsed light. One disadvantage of the above described devices is that the power (both electrical and light output) required to deliver permanent or long lasting results are extremely high, and such devices are only suitable for use in a clinical setting with trained professionals operating the devices. A further disadvantage is that the treatments are costly, painful, time consuming and only partially effective. To improve efficacy of these treatments more and more powerful devices have been marketed in an attempt to produce long lasting results. Additionally these devices utilize large diameter output beams which are known to penetrate the skin deeply and to deliver high doses of energy to the base region of the hair follicle. These newer devices which are capable of generating the "required" power level for effective long-term hair loss using large diameter spots are large, heavy, expensive, require sophisticated cooling, and are dangerous. Current prices on the market for such devices exceed $50 K and the device itself can weigh more than 100 lbs. These are not devices that can be sold to individual consumers, or be operated safely in the home by average consumers.

In addition to the production of more powerful laser devices, a trend has also emerged toward larger spot sizes. Experimental results have shown that larger spots penetrate more deeply into tissue than small ones. Thus, researchers in this area, in an effort to obtain a long-lasting and more permanent result, strive to provide the larger sizes. Until now, little research has gone into understanding the actual behavior of light as it diffuses into tissue as it relates to the spot size. As a result, the use of small spot treatments has been dismissed as not feasible in this area of dermatology.

The commonly held (though incorrect) understanding of how light diffuses into skin as a function of spot size has prevented the industry from developing effective methods for hair growth modulation for the end consumer. The belief that only large diameter laser and IPL spots can cause hair loss has lead the entire industry to develop larger, more expensive and more dangerous devices; now producing more than 2900 W of output power.

The disclosed technology relates to methods and devices that use a model for light diffusion in skin as a function of spot size. These methods and devices use a small spot size and low power radiation to achieve short-term hair growth modulation as well as for the treatment of other skin disorders. Furthermore the disclosed technology can be incorporated into a device which can be highly effective using a fraction of the power required by today's typical devices. The device disclosed herein can be mass produced for safe use in the home with excellent results.

SUMMARY

In one illustrative embodiment, the disclosed technology is embodied within a system adapted to perform a selected dermatologic treatment. Such a system can include a light pipe that is optically coupled to a source of light energy suitable for the selected dermatologic treatment, wherein the light pipe conveys at least some of the light energy to a first target treatment location on a person's skin. A scanner that is mechanically coupled to the light pipe changes an orientation of the light pipe to facilitate the application of the conveyed light energy to subsequent other locations on the person's skin.

In another illustrative embodiment, the disclosed technology is embodied within an optical system adapted to temporarily affect the hair growth on a patient's skin. This optical system includes a laser bar that produces light energy appropriate for affecting hair growth on the patient's skin. A light pipe that is optically coupled to the laser bar conveys at least some of the light energy to a first target region on the patient's skin, and the orientation of such light pipe can be changed to convey light energy to subsequent other locations on the patient's skin using a mechanically-coupled scanning mechanism having, for example, a shaft with two helical grooves.

In yet another illustrative embodiment, the disclosed technology is embodied within an optical head, which includes a source of light energy and a light pipe optically coupled to the source and adapted to convey at least some of the light energy to a first target location. The optical head can also include a scanner that is mechanically coupled to the light pipe and that is adapted to change an orientation of the light pipe to convey light energy to subsequent other target locations. The light pipe and scanner are preferably contained within the optical head in this embodiment.

In yet another illustrative embodiment, the disclosed technology can be embodied within an optical head, which includes a source of light energy and an optical element optically coupled to the source and adapted to convey at least 95% of the light energy to a first target location. The optical head can further include a scanner that is mechanically coupled to the optical element and adapted to change an orientation of the optical element so that the conveyed light energy is directed at subsequent other target locations. The optical element and scanner are preferably contained within the optical head in this embodiment.

BRIEF DESCRIPTION OF THE DRAWINGS

The foregoing discussion will be understood more readily from the following detailed description of the disclosed technology, when taken in conjunction with the accompanying drawings in which:

FIG. 14d is an enlarged portion of the diagram of FIG. 14a;

DETAILED DESCRIPTION

Unless otherwise specified, the illustrated embodiments can be understood as providing exemplary features of varying detail of certain embodiments, and therefore, unless otherwise specified, features, components, modules, elements, and/or aspects of the illustrations can be otherwise combined, interconnected, sequenced, separated, interchanged, positioned, and/or rearranged without materially departing from the disclosed systems or methods. Additionally, the shapes and sizes of components are also exemplary and unless otherwise specified, can be altered without materially affecting or limiting the disclosed technology.

For the purposes of this disclosure, the term "substantially" can be broadly construed to indicate a precise relationship, condition, arrangement, orientation, and/or other characteristic, as well as, deviations thereof as understood by one of ordinary skill in the art, to the extent that such deviations do not materially affect the disclosed methods and systems.

The theory of light diffusion in scattering media is used to determine the amount of fluence needed to have a cosmetic effect on the skin. In the near IR spectral region the absorption coefficient for skin is $\mu_a = 0.02$ mm$^{-1}$. This coefficient gives the number of events of absorption for an average photon traveling along a 1-mm path. The reduced scattering coefficient for skin is $\mu'_s = 1.6$ mm$^{-1}$. This coefficient determines the number of events of photon isotropic scattering on the same path. Thus the possibility of a photon scattering is about 2 orders of magnitude higher than for its absorption. That is why the light propagation in skin is described by diffusion equation rather than by regular wave theory.

Figure 1:
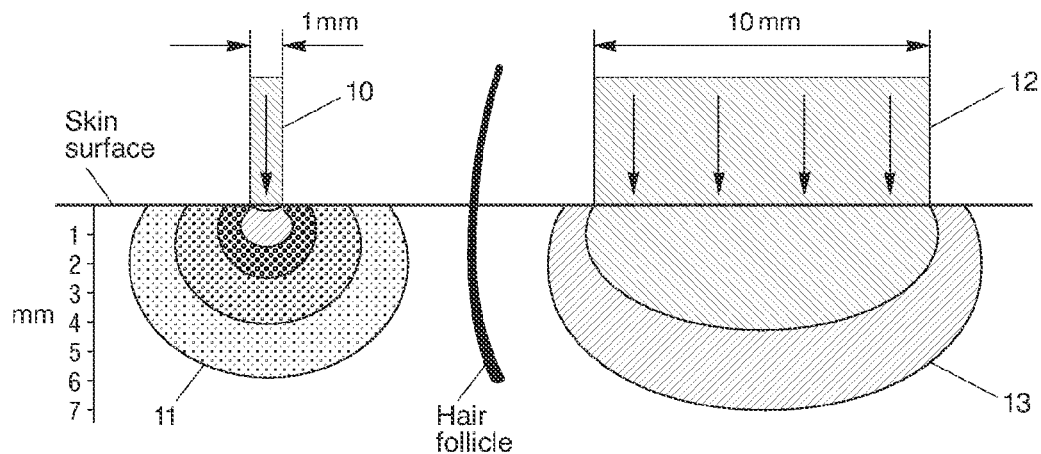
FIG. 1 is a schematic diagram of the relationship between spot size and penetration depth for illumination on human skin.
Figure 2:
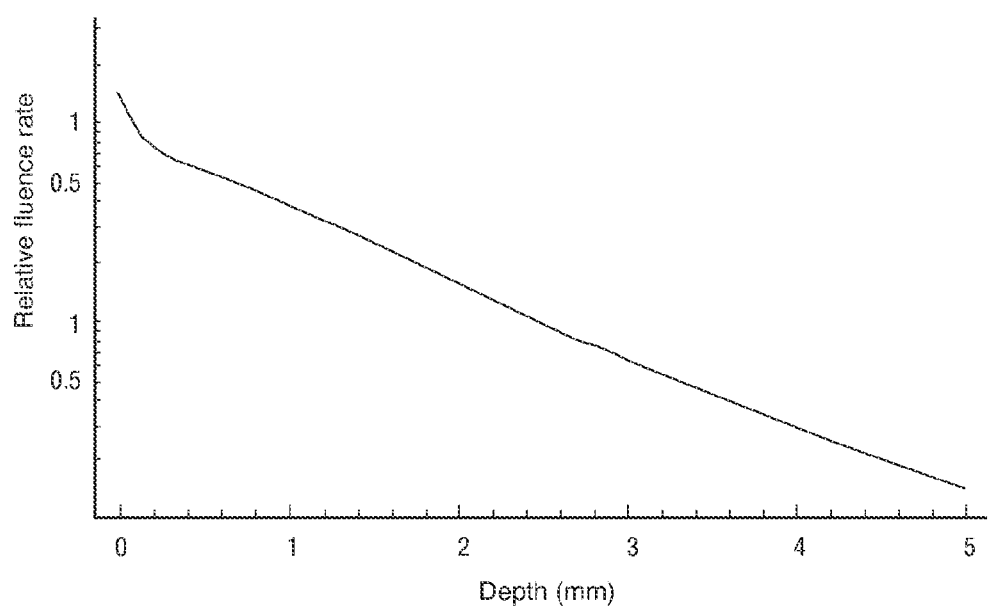
FIG. 2 shows the decrease of fluence rate with depth along a beam axis for a 1-mm beam.

Referring to FIG. 1, two laser beams of equivalent power density or irradiance are seen in cross section penetrating a skin region with a hair follicle shown for scale. The first beam 10 is narrow and as a result its power will diffuse into the skin near to the surface forming a pattern roughly as outlined. The drawn contours 11 correspond to the fluence rate levels (W/cm$^2$) of 1.0, 0.3, 0.1, 0.03, and 0.001 times the surface radiance. The contours 13 of the larger beam 12 correspond to fluence rate levels of 1.0 and 0.3 times the surface radiance. The larger beam 12 clearly shows that at predetermined depth it is able to deliver power close to the original power, while the narrow beam 10 shows that at the same predetermined depth its delivered power is a fraction of its original power. Generally to achieve a cosmetic result, such as a short-term hair growth, the predetermined depth is 1-6 mm below the surface and the delivered fluence at 1-6 mm below the surface is 0.1-10 J/cm$^2$. FIG. 2 shows the rapid decrease of fluence with depth along the beam axis of a one mm beam.

But if the total power of both beams that is required to provide the same fluence at the desired depth is considered, the advantage of narrow beam will be seen. As known from light diffusion theory, the fluence $\Phi_1$ far from the surface is described by the equation:

$$\Phi_1 = \frac{3\mu_s'}{4\pi} P_1 \frac{\text{Exp}\left[-\sqrt{3\mu_s'\mu_a}\,(z-1/\mu_s')\right]}{z-1/\mu_s'} \quad (1)$$

where z is the depth and $P_1$ is the power of light source. Referring again to FIG. 2, the fluence from a one mm beam has an exponential behavior at a depth of more than one mm, therefore showing that the behavior of the beam can be described by equation (1). The surface fluence rate provided by the broad beam can be expressed as:

$$\Phi_2 = P_2/\pi R^2 \quad (2)$$

where $P_2$ is total power delivered by the beam, and R is the radius of the broad beam.

If the right parts of equations (1) and (2) are equated, how much power is required by a large beam versus a small beam to achieve the same fluence at a desired depth can be determined. The ratio of $P_1/P_2$ is then given by:

$$\frac{P_1}{P_2} = \frac{4(z-1/\mu_s')}{3\mu_s' R^2} \text{Exp}\left[\sqrt{3\mu_s'\mu_a}\,(z-1/\mu_s')\right] \quad (3)$$

Figure 3:
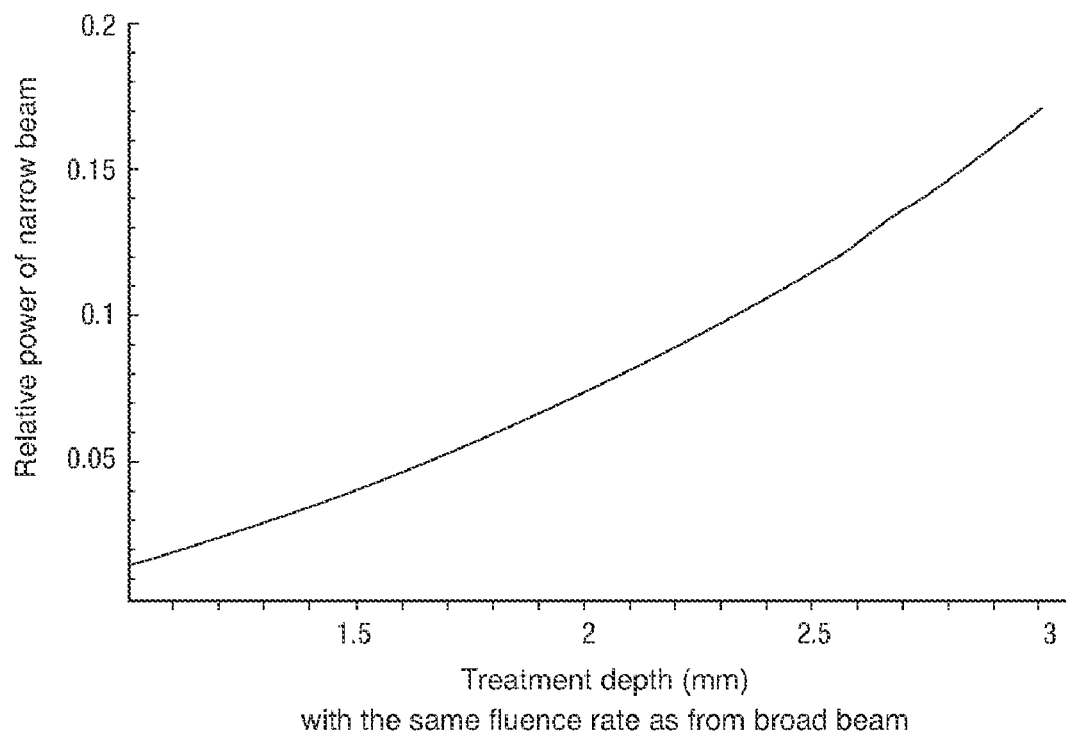
FIG. 3 is a graph of relative power of a narrow beam plotted against depth showing the relative power of a small beam compared to a wide beam having the same fluence.

Equation (3) describes the fraction of broad beam power that a narrow beam must have to deliver the same fluence to the depth z as is delivered by a large beam of radius R. FIG. 3 illustrates a plot of this equation for R=5 mm (beam diameter 10 mm), and $\mu_s'$=1.6 mm$^{-1}$, $\mu_a$=0.02 mm$^{-1}$ corresponding to human dermis.

FIG. 3 demonstrates that for all depths within the range of interest the power of narrow beam is much less than that required for 10 mm beam. The power required to deliver specific fluence to the mean depth of 3 mm is next calculated using a fluence level of 1.5 J/cm$^2$. It is determined that for a broad beam to deliver 1.5 J/cm$^2$ to the target, the original beam should also be 1.5 J/cm$^2$ since little power is lost at the relevant depths. If the beam has a diameter of 10 mm then the total area of the beam is 78.5 mm$^2$ and the total delivered energy is 1.18 J. If the pulse duration (length of time the target is directly illuminated) is equal to 30 ms (a fairly standard pulse duration as known in the art), then the output power of the broad beam device must be 39 W. From equation (3) and FIG. 3, the same fluence will be delivered to a three mm depth by narrow beam using only 6.8 W of power. Thus the narrower beam requires that less power be developed for the same effect.

It is known in the art that laser diodes are a good way to develop laser beams for such dermatological treatments. It is also known that diode lasers have a limited power output per chip, and to develop high power so called "diode laser bars" are utilized. These laser bars are a sequence of many diode lasers which then use optics to combine the numerous output beams into a single more powerful beam. With present technology a single laser diode chip may only be able to produce up to 7 or so Watts of power. If more power is needed then the cost of producing such device will grow dramatically due to the optics needed to combine the beams; the added cost for producing a bar rather than a single chip; and the larger power supply needed to power such a system.

By discovering that certain effects such as short term hair growth modulation are actually possible at low fluences, and by determining the actual behavior of light as it diffuses in skin, the disclosed technology pertains to a method and apparatus to cause a cosmetically valuable result such as the retardation of hair growth with very low power. A device capable of employing this method can be produced very inexpensively and can also be manufactured in consumer quantities. Furthermore, because the disclosed technology incorporates a low fluence methodology, only a single laser diode is needed and hence the total cost of the device is further reduced because the optics for beam shaping is simplified by using a laser diode chip that is a "point" light source. This single low power laser device also simplifies the electronics and mechanical requirements by lowering the power needed and eliminating many optical stages for collimation and shaping.

The disclosed technology also takes advantage of a further innovation in which the small beam is moved across the skin to treat large areas. In the prior art the high power small beams were held in position over a precise target such as a single hair by an apparatus. In some cases, an actual optical fiber was introduced into the follicle to deliver the treatment beam. By moving the beam across the skin and harnessing the diffusive behavior of the light in scattering media the operator can now treat large areas rapidly.

Figures 4A, 4B:
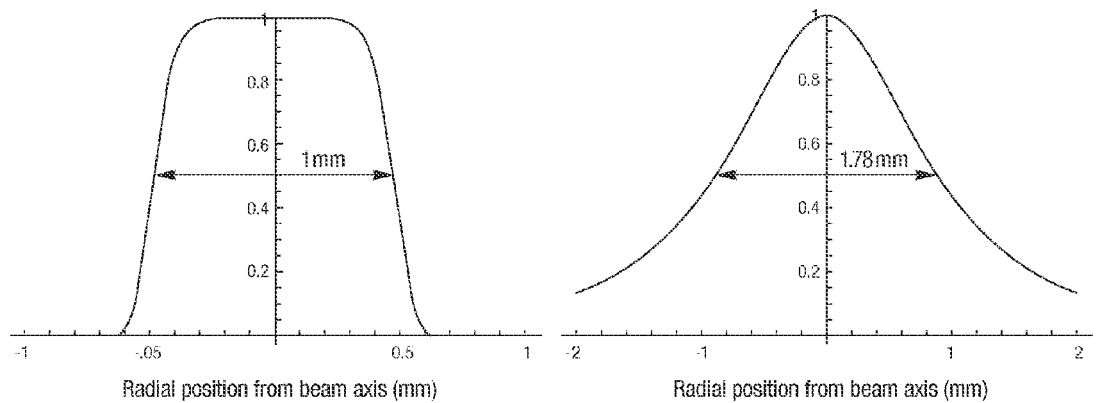
FIGS. 4(a-d) are graphs of the relative fluence generated by a one mm beam passing through skin to different depths.
Figures 4C, 4D:
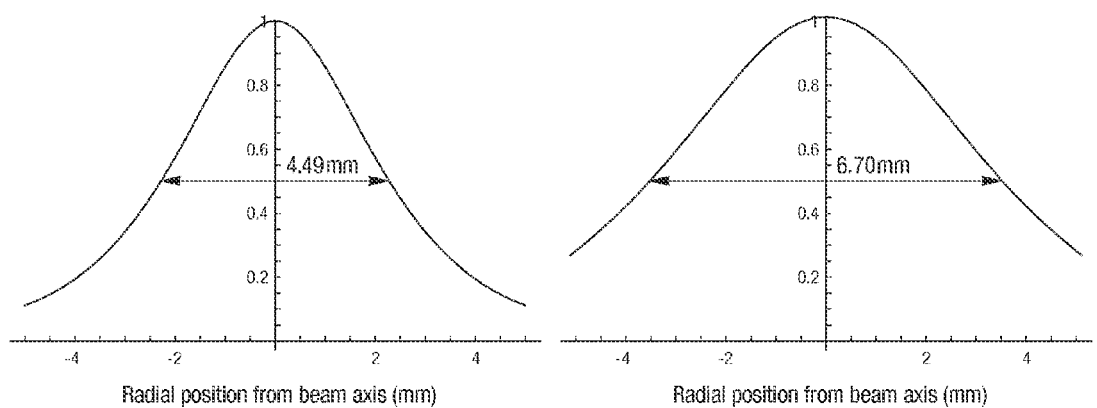
Figure 5:
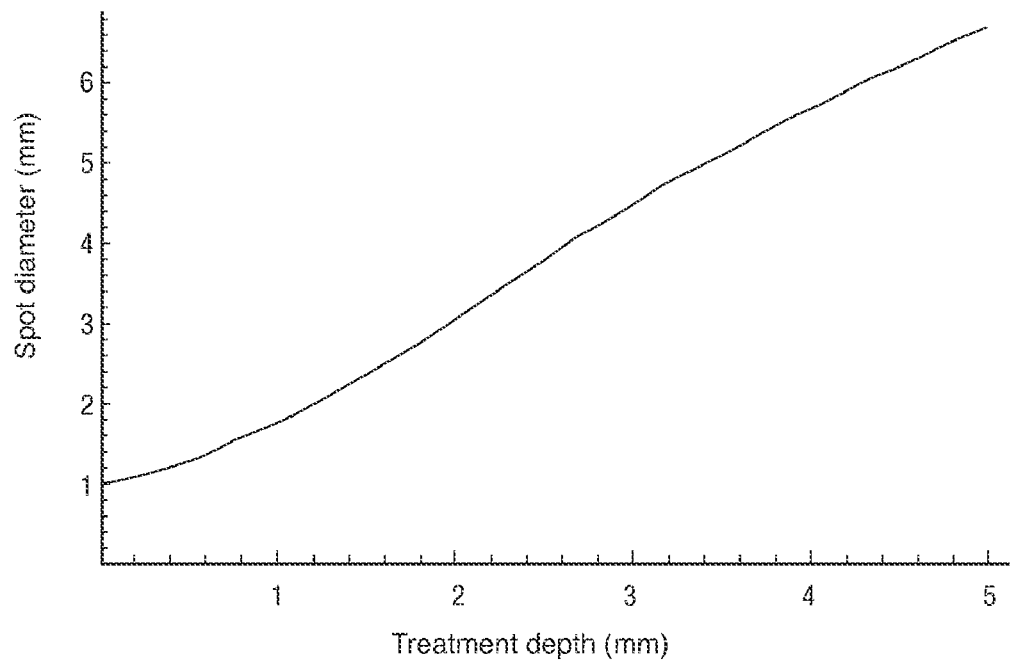
FIG. 5 is a graph showing the relationship between spot diameter and treatment depth.

Referring to FIG. 1 again, in the case of the narrow beam 10, the model shows that the actual diameter of the treatment area below the skin surface is much larger than the diameter of the original beam. This is not so in the case of the wide beam 12. This conclusion is confirmed by a calculation of the fluence distribution at different depths, which are generated by a narrow beam. FIGS. 4 (a-d) show the fluence profile produced by 1-mm beam at the depths: 0, 1, 3, 5 mm. In this figure, all curves are normalized to the axial fluence at the same depth. The absolute values of axial fluence are depicted in FIG. 2. The diameter of an illuminated spot at each depth can be determined as Full Width at Half Maximum (FWHM) of the curve. FIG. 5 shows the continuous dependence of spot diameter on the depth for 1-mm beam.

Figure 6:
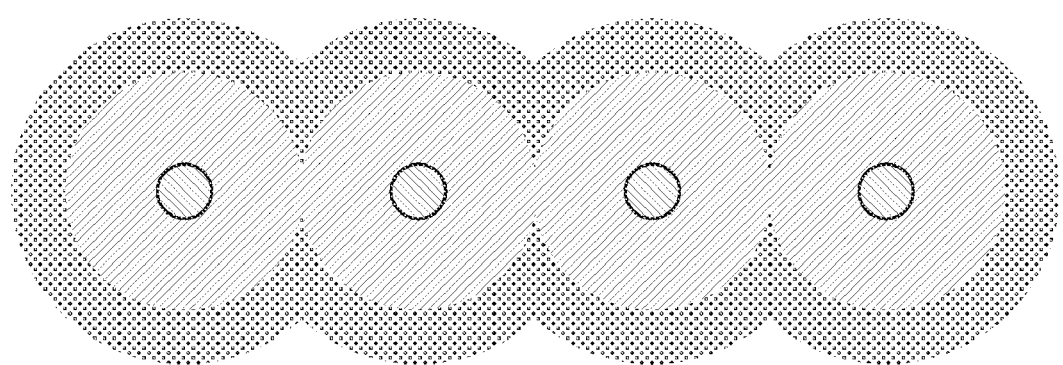
FIG. 6 is a schematic diagram of non-continuous treatment over an area of skin.

By utilizing the behavior of the beam as it penetrates the skin, the disclosed technology is able to function in such a way as to separate the concepts of direct illumination and treatment area. In other words, the disclosed technology utilizes the new discovery that when using a small spot, the treatment area is substantially larger than the illuminated beam diameter on the surface. Referring now to FIG. 6, a plan view of a treatment area is shown that takes advantage of the fact that a larger area is treated at the desired depth than is directly illuminated on the surface. Using a non-continuous movement across the skin surface, this fact enables treating a continuous area while only directly illuminating a fraction of the total area. Also, by using the method of substantially continuous movement across the skin, it is possible to reduce the time needed for treatment by increasing the rate of movement and decreasing the time of direct illumination while still achieving good efficacy. It is easily understood that it is advantageous to reduce the time needed for direct illumination, while covering large areas quickly. The time between pulses may be selected to allow the skin to cool so as not to damage areas of the skin not under treatment (for example areas adjacent the hair follicle being removed).

A further aspect of the disclosed technology is the substantially continuous movement of the beam across the surface while in CW or continuous wave mode. Prior art systems typically use Pulse Mode (PM) for treatment in which the device fires a high power pulse of light to treat an area. This has several disadvantages. One disadvantage is the non-linear behavior in power output as laser systems energize and come to equilibrium. As a result, the amount of energy delivered to the target is not constant, nor is it easily calibrated. Furthermore, in prior art systems with large diameter beams utilizing PM, the operator physically moves the device a step at a time prior to exposing the skin to a pulse of light. This is cumbersome, and also introduces the likely result of not treating areas completely due to human error of moving the device in irregular steps, unlike in the disclosed technology in which scanning of the beam occurs automatically.

Figure 7:
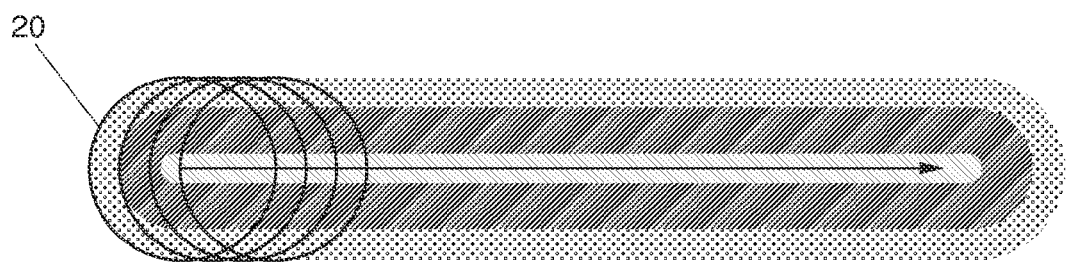
FIG. 7 is a schematic diagram of continuous treatment of an area of skin.

Pursuant to the disclosed technology, in either the CW case or the scanned PM case, the treatment time (TT) or the amount of time an area is treated, can be calculated either as the length of time the beam directly illuminates a point on the surface as it passes by, or by the amount of time the subcutaneous area is treated directly or indirectly through the diffusive properties described above. FIG. 7 shows the treatment area using a narrow beam continuous wave laser. The area that can be treated using this method is larger than the area covered by direct illumination. In FIG. 7 the series of circles shows that the area which can be treated over time is different from the amount of time any area of skin spends under direct illumination. In the very first circle of treatment 20, one can easily see that some of the areas being treated have not been illuminated directly at all.

Continuous movement of an illumination spot over a surface provides an additional advantage relative to a pulse mode source. The treatment efficiency depends on the total fluence [J/cm$^2$] delivered by the beam to the treated area, rather than on its fluence rate [W/cm$^2$].

When treatment is provided by a stable spot from a pulsed source, the distribution of both of these parameters inside the treated medium is the same because the treatment area depends on the beam width. As an example, in this case the fluence from the laser beam of 1 mm diameter will depend on the depth as shown in FIG. 2.

However, if illumination is provided by a CW source and the spot is moved across the surface, the duration of treatment is determined by scanning speed and spot diameter. The last parameter grows with the depth because of light diffusion. Therefore, the treatment duration increases with depth in the same manner as the spot diameter. As fluence is the product of the fluence rate and the pulse width, it decreases slowly with the depth compared to the fluence rate.

Figure 8:
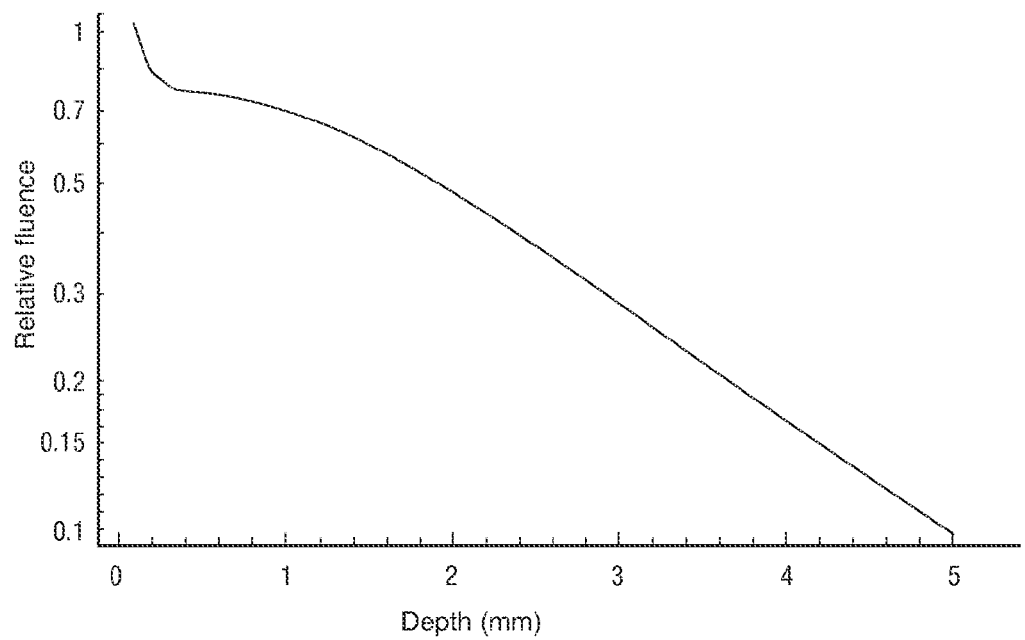
FIG. 8 is a graph depicting the dependence of fluence on depth for the surface beam diameter of 1 mm.

FIG. 8 shows the dependence of fluence on depth for a surface beam diameter of 1 mm. The curve is calculated as a product of functions shown in FIG. 2 and FIG. 5. From a comparison of FIGS. 2 and 8 it is seen that fluence is decreased by 10 times at the 5 mm depth, while fluence rate drops almost to 1% of the surface amount at the same depth. Therefore, the amount of fluence delivered to the 5-mm depth from moving CW beam is higher by almost 10 times than from the stable pulsed beam, if surface fluence is the same in both cases.

Figure 9:
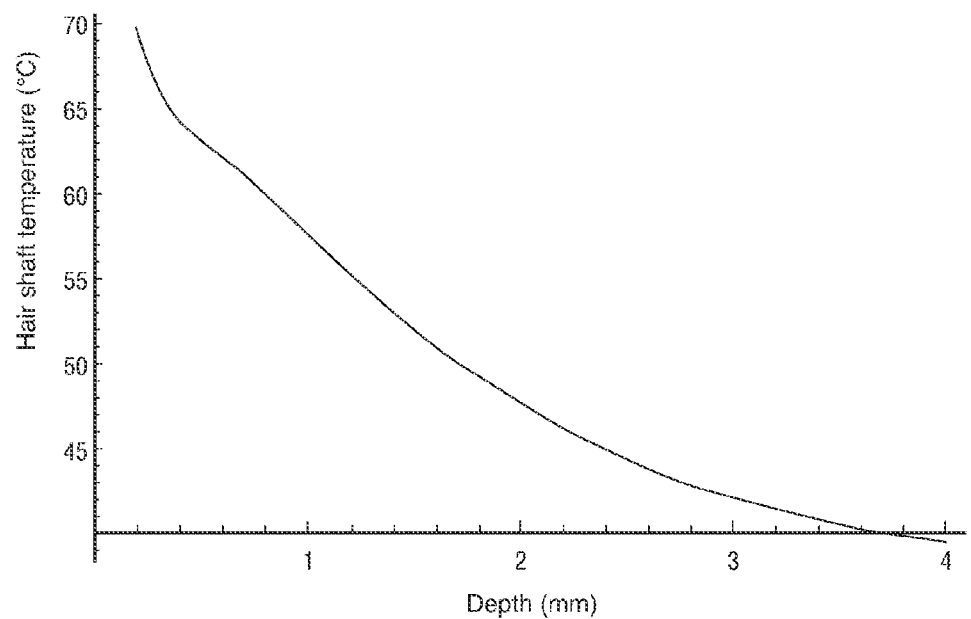
FIG. 9 is a graph depicting the distribution of the highest temperature along the dark hair shaft produced by a moving narrow beam.

A further aspect of the disclosed innovation is that, unlike what is described in the prior art intense treatment of the base of the hair follicle, or the papilla, may not be needed to gain a cosmetic result. The disclosed innovation is based on the discovery that treating the upper and mid-portion of the follicle may be sufficient to cause hair growth modulation. FIG. 9 illustrates the distribution of temperature along a dark hair shaft, which is produced by 1.5 W beam with 1-mm of surface spot diameter moving with the speed of 100 mm/sec. From this graph it is seen that the upper portions of the hair are brought to a higher temperature. The temperature of portions of the hair located deeper than 3 mm is below 42° C. This keeps those portions from being severely damaged. The hair bulb is generally positioned deeper than 3 mm from the skin surface.

It should be noted that for broad beams the depth discrimination is achieved using shorter wavelengths. This is because the penetration depth of light is strongly decreased with shortening wavelengths because of scattering and absorption. This is different with the use of a narrow beam where penetration is controlled by the geometry of illumination rather than the wavelength of light.

Figure 10:
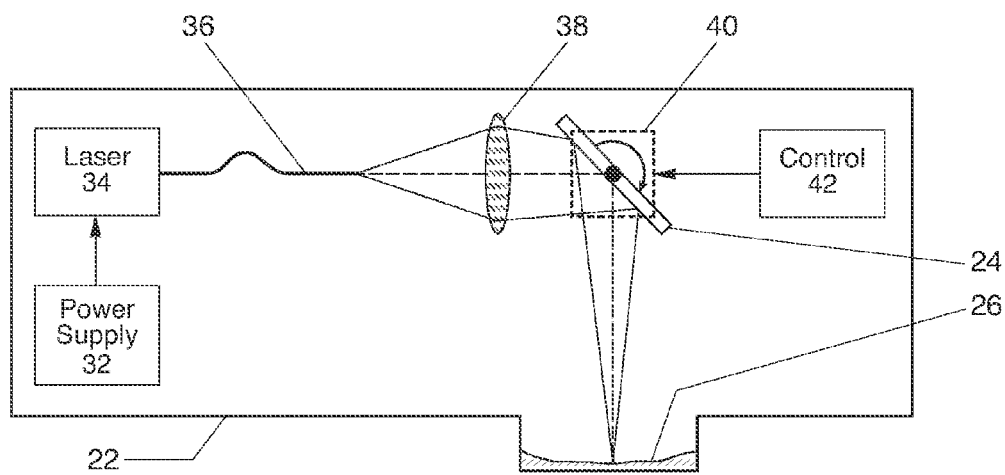
FIG. 10 is an embodiment of a treatment device constructed in accordance with the disclosed technology and using a galvanometric mirror as a scanning device.

Referring to FIG. 10, to implement this method of hair growth modulation, a hand-held optical head 22 containing a laser 34 and an optical system which distributes laser beam over a diameter of about 1 mm on the output window 26 may be used. The window 26 is preferably placed in direct contact with skin. To provide the short treatment duration, the laser either works in continuous wave (CW) mode with simultaneous movement of the focused spot or in pulse mode (PM).

The speed of movement (V) of the spot over the treatment area for CW mode is determined by the desired amount of pulse width ($\tau$) and the diameter of treated area (D):

$$V = D/\tau \tag{4}$$

When the diameter of a directly illuminated spot (d) is small, the diameter of the treated area is larger because of light diffusion, as shown in FIGS. 4-7. For d=1 mm, the factor of increase K is between 1 and 4 depending on treatment depth. The exact amount of factor K for any depth is shown in FIG. 5. Therefore, to provide a common pulse width ($\tau$=30 ms), the optical head should be moved with the speed:

$$V = Kd/\tau \tag{5}$$

within the range (33~133) mm/sec. The speed for other pulse widths ($\tau$) is determined by equation (5).

Figure 11:
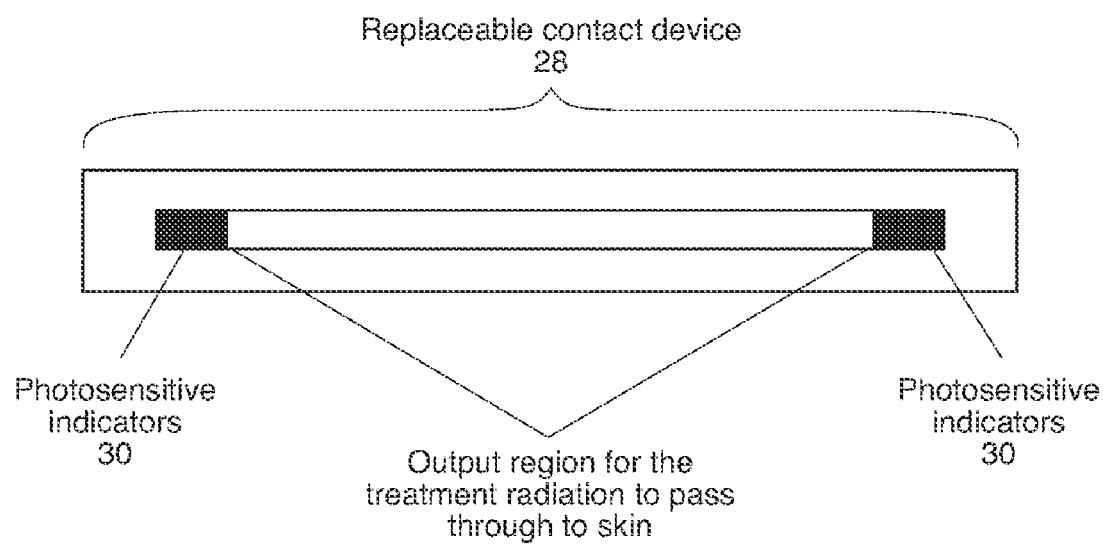
FIG. 11 is an embodiment of a contact device as constructed in accordance with the disclosed technology.

In one embodiment, the window 26 of the apparatus incorporates a replaceable transparent contact device 28 (FIG. 11) that is able to perform multiple functions. In one embodiment the replaceable contact device is in the form of a flat plastic (or other suitable material) covering that protects the apparatus from contaminants such as skin oils, dander, cosmetics, or other undesirable materials. Additionally since the preferred means of operation calls for the apparatus to be drawn across the skin repeatedly, the hair shafts as well as the skin itself will cause abrasions to the contact device which will impair the transmission of the treatment radiation from passing efficiently into the treatment area of the skin. The prior art systems tend to employ expensive abrasion resistant materials such as sapphire, fused silica, or other rare and exotic materials in a permanently affixed output window. For reasons of efficacy it is desirable to have the contact device remain abrasion free such that the treatment radiation is able to maintain as close to loss-less transmission into the skin as possible.

One illustrative embodiment includes a replaceable contact device that is discarded after a predetermined number of uses. This replaceable contact device is shown generally in FIG. 11. In another embodiment, the replaceable contact device includes areas of material that are photosensitive 30 such that after a predetermined amount of radiation energy is absorbed by these elements, the color or visible characteristics are modified to be an indicator to the operator that the contact device should be replaced. In yet another embodiment a sensor in the apparatus monitors the amount of treatment radiation that has been transmitted through the contact device since it has been installed and causes an indicator to indicate to the operator when the replaceable contact device should be replaced to maintain proper efficacy.

In still yet another aspect of the disclosed technology the sensor is mounted in the apparatus and the replaceable contact device is configured to enable the sensor to pass through the window to make contact with the skin proximal to the treatment area. If the sensor is not mechanical, but is optical or other means not requiring contact with the skin proximal to the treatment area, the window can be properly shaped to enable the correct configuration of the sensing field to be passed through into the proximity of the treatment region. In still yet another embodiment the sensor is a part of a circuit that detects if the sensor is not in close proximity to the skin and if not, turns off power to the light source. This interlock reduces the likelihood of eye damage by preventing the beam from forming if the skin is not in a position to absorb the light radiation. The risk of eye damage can also be mitigated by incorporating an optical diffuser in the output window 26. In one illustrative embodiment, the optical diffuser forms the outer surface of the output window which comes into contact with the treatment area. Exemplary optical diffusers that may be used within the disclosed systems can be as further described in U.S. patent application Ser. No. 10/783,880, the entirety of which is incorporated herein be reference.

In an illustrative embodiment, the laser spot is linearly moved back and forth across the output window of the device by a scanning system incorporated in the optical head. The amount of scanning speed is selected in accordance with equation (5). Movement of the device in a direction perpendicular to this periodic scanning direction can be performed manually or automatically, such as by rotating wheels affixed to the device and in contact with the skin during the treatment thereof.

Figure 12:
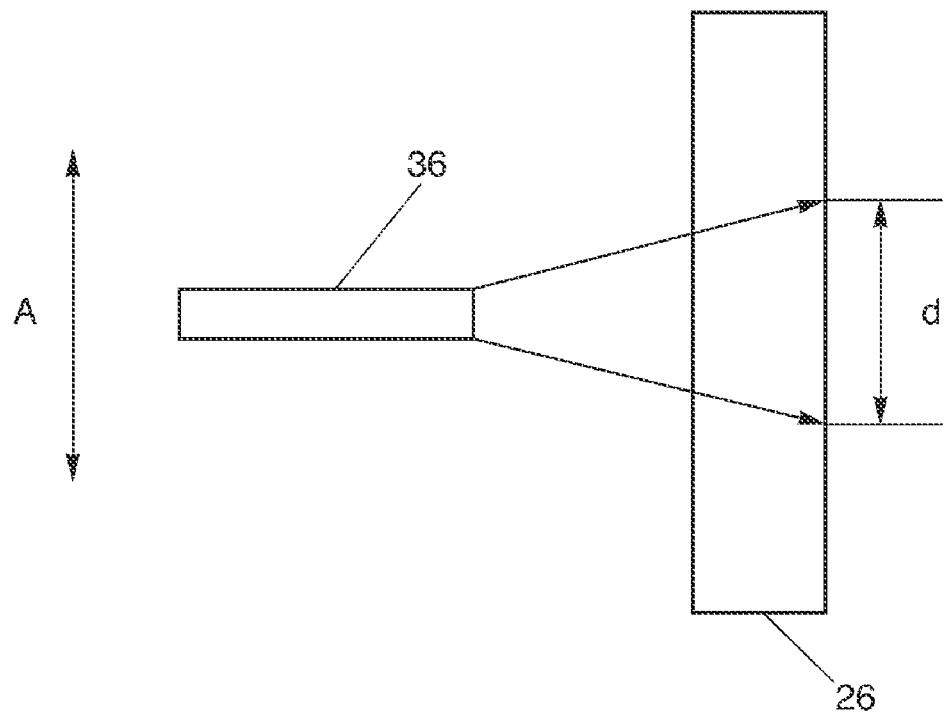
FIG. 12 is another embodiment of a scanning device using a moving optical fiber.
Figure 12A:
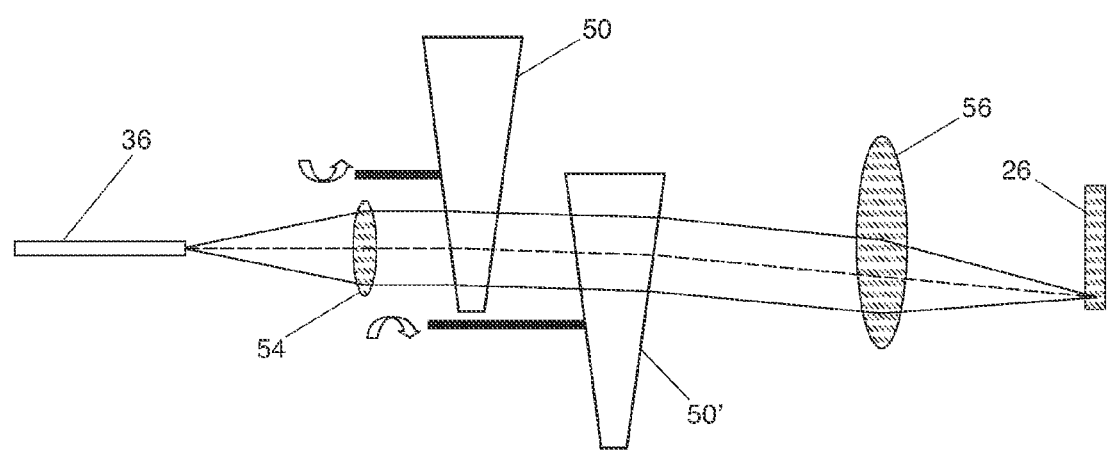
FIG. 12a is yet another embodiment of a scanning device using rotating wedges.
Figure 13:
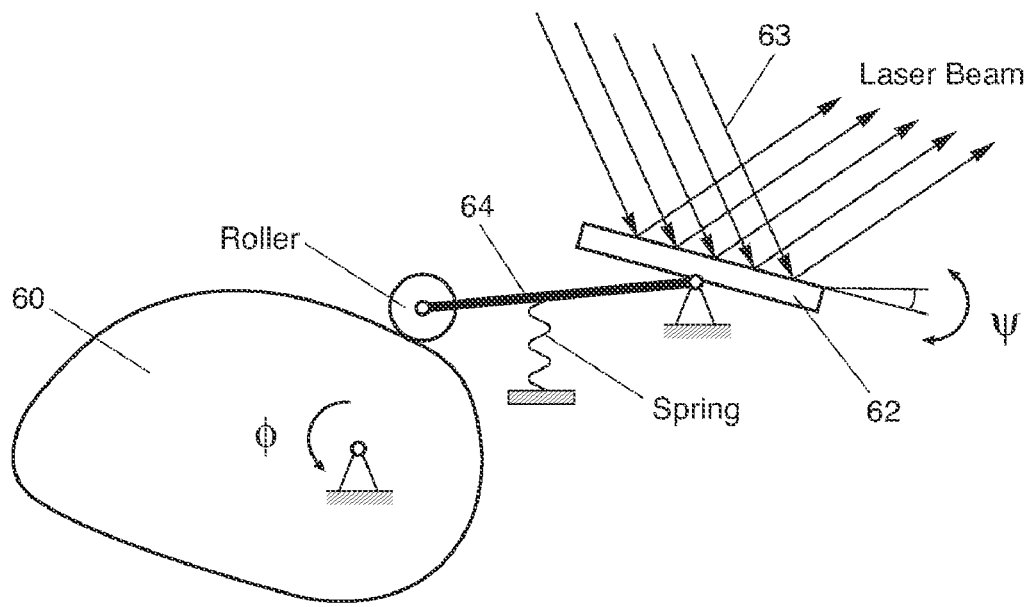
FIG. 13 is yet another embodiment of a scanning device using a cam.
Figure 14:
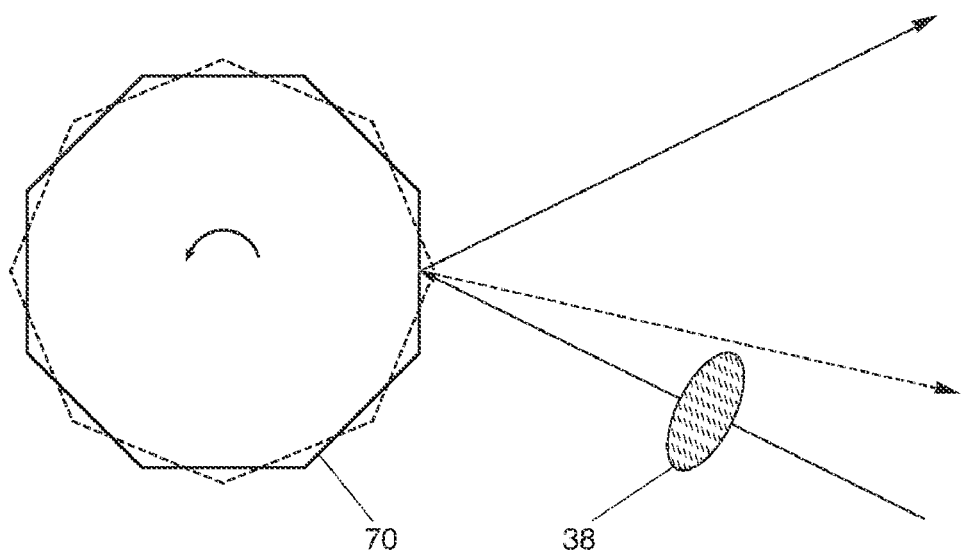
FIG. 14 is still yet another embodiment of a scanning device using a rotating polygon.

In general, the methods for optical beam deflection which can be utilized in the disclosed technology to provide one-dimensional scanning of the output spot can be divided generally into five classes: light reflection from periodically moved surfaces; light refraction by periodically moved transparent bodies; periodic movement of the light source; light diffraction by ultrasound waves and light refraction in crystals controlled by varying electric field. Some embodiments utilizing some of these classes of scanning systems are described below. In particular FIGS. 10, 13, and 14 are embodiments of reflective systems; FIG. 12 is an embodiment of a system involving periodic movement of the light source; while FIG. 12a is an embodiment of a refractive system.

Referring again to FIG. 10, a scanner based on an oscillating mirror controlled by a galvanometric system is shown. A power source 32 supplies current to a laser 34, which delivers the laser light to the hand-held optical head 22 by means of an optical fiber 36. Light from the fiber 36 is expanded by an optical lens system 38 to the desired diameter and projected to an output window 26 after being reflected by an oscillating mirror 24. The oscillating mirror is moved by a galvanometer 40 under the control of a control system 42. The output window 26 can be made as a cylindrical plano-concave lens to serve as a field flattener.

In one embodiment the power supply 32 draws its power from an electric outlet. In another embodiment, the handheld device 22 includes batteries. It is well known that the power requirements of today's laser output devices such as diode or solid state lasers are beyond the limits of off-the-shelf standard battery types. In one embodiment the disclosed technology is designed for use with specially adapted, high-output batteries employing technology such as Ni Cd which are possible to develop to discharge their entire power supply in a short period of time with high output power. In one embodiment, the apparatus is calibrated to use a fast discharge, replaceable battery component that the operator can easily remove and replace or recharge. The apparatus disclosed here also contains a monitoring means for tracking the level of power in the battery unit to ensure that enough power is available to provide a therapeutic radiation level. This monitoring means will also be configured to read information stored in the battery to ensure that it is the proper type so as to avoid powering the apparatus with an unsuitable battery that may cause damage to the device. By providing a microcontroller or other suitable logic that is able to monitor the identity and parameters of the high output battery supply the operator can be assured of proper operation and satisfactory results.

In another embodiment the battery is fitted with specifically shaped contact points and an overall shape such that only properly designed or "authorized" batteries can be fitted into the apparatus. Due to the complicated internal workings of the small field radiation device it is preferable that the device be fitted with a conforming power source such that the correct amount of output radiation can be expected. It is well known that the output power of diode type laser chips, such as those disclosed for use in the disclosed apparatus, have output power in proportion to the input power. It is clear that a battery source having too high an output could cause burns in the skin region of the user.

FIG. 12 shows an embodiment of the handheld device and the scanning system with minimal optics. In this embodiment the laser light is again delivered by an optical fiber 36 whose tip is mechanically moved back and forth (arrow A) across the output window 26 by an actuator (not shown). As the light diverges from the end of the fiber, the desired spot size is formed. In one embodiment the actuator is substantially the same as is used in computer disk drives.

FIG. 12a shows an embodiment of beam scanning provided by two similar transparent 50, 50' wedges preferably rotating with the same speed in opposite directions. The laser beam is collimated by lens 54 and passes sequentially through two wedges, which deflect it by a changing angle as the wedges rotate. An objective lens 56 transforms the varying incident angles into the different positions of the focused spot on the output window 26.

FIG. 13 shows another embodiment of the scanner based on a rotating cam 60; a non-round cylinder eccentrically positioned on the motor axis. The cam 60 mechanism provides the conversion of uniform motor rotation into angular reciprocation of mirror 62. The scanning of the laser beam 63 is achieved by its reflection from the oscillating mirror 62. The angular movement of rocker 64 is determined by the cam 60 profile and its rotational speed because cam 60 and rocker 64 are in permanent contact provided by roller and spring. Mirror 62 is connected to rocker 64 and has a common rotational axis. The angular mirror position depends on the rotational angle of cam 60. The working range is limited by linear part of the curve when the output angle of light reflected from the mirror is uniformly increased with angular motor position (and correspondingly, with time). After the end of each working cycle, the mirror is quickly returned to the initial position. This is necessary to provide unidirectional beam scanning. The ratio of working range angle to the full rotation angle of 360° gives the amount of duty cycle. It should be noted that it is possible to provide a scanning mechanism which permits the beam to be scanned in both directions.

FIG. 14 shows another embodiment of the scanner based on the beam reflection from a rotating polygon 70. The polygon 70 can be a prism having a mirrored surface. This is a compact design, which in addition to being compact, is free from mechanical vibrations produced by other presented embodiments.

In more detail, the characteristics of a polygon-based embodiment may be derived from some general input parameters. Referring to FIGS. 14a-d, in each figure (NA) is the numerical aperture of a fiber; (M) is the linear magnification; D is the polygon diameter; α=360°/n which is the angle between neighboring faces of polygon (where n is the number of faces); γ is the angle of light incidence to the polygon face in the perpendicular plane to the rotational axis for the middle point of the scanning line; L is the scanning length; d is the output spot diameter and C is the duty cycle for the spot scanning.

Figure 14A:
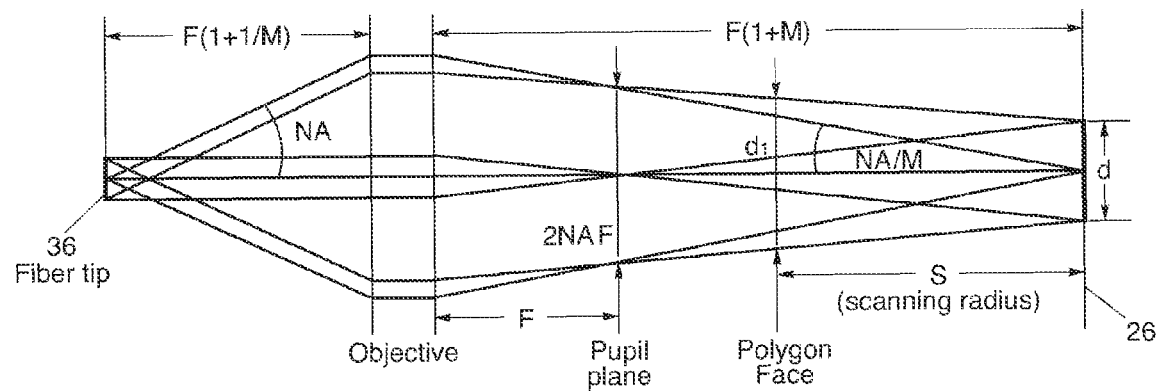
FIG. 14a is a ray diagram of a paraxial model of an embodiment of the polygon-based scanner of FIG. 14.

FIG. 14A shows a paraxial optical model of the polygon based scanner. Laser light is delivered into system by fiber 36, which tip is imaged with magnification (M) onto the plane of output window 26 within the spot diameter (d). The objective is described by two cardinal planes. The chief and marginal rays are shown for central and edge points of fiber tip. As chief rays are parallel to the optical axis, the pupil is positioned in the back focal plane of objective. (d.sub.1) is the beam diameter at the polygon face.

Figure 14B:
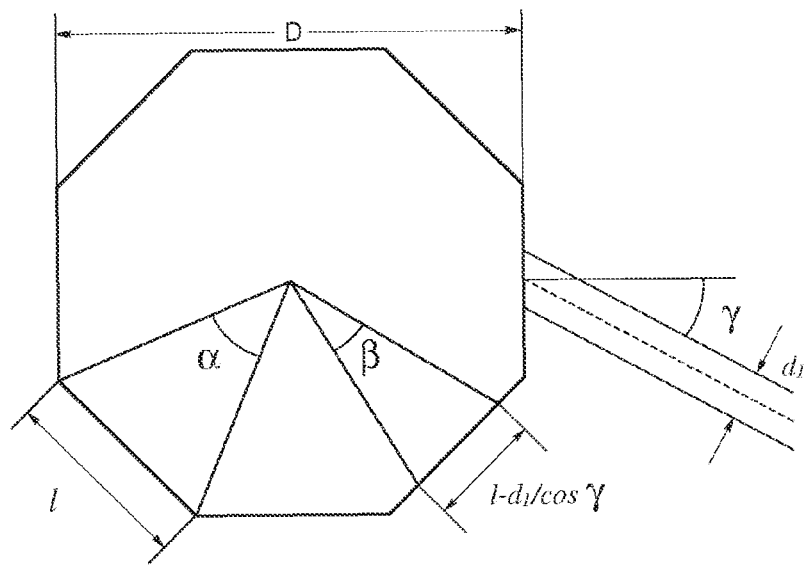
FIG. 14b is a schematic diagram of an embodiment of the polygon of FIG. 14 showing various geometric features.

FIG. 14b shows the polygon geometry that allows derivation of the following:

The facet length is given by the equation:

$$l = D \tan(\alpha/2) \qquad (6)$$

Duty cycle (C) is defined as the useful fraction of the scanning period when the laser beam is completely reflected by the polygon face without truncation by its edge:

$$C = (l - d_1/\cos \gamma)/l \qquad (7)$$

The scanning angle (β) is given by:

$$\tan(\beta/2) = C \tan(\alpha/2) \qquad (8)$$

The beam diameter (d.sub.1) at the polygon face is derived from equations 6 and 7:

$$d_1 = D \cos \gamma (1 - C) \tan(\alpha/2) \qquad (9)$$

Figure 14C:
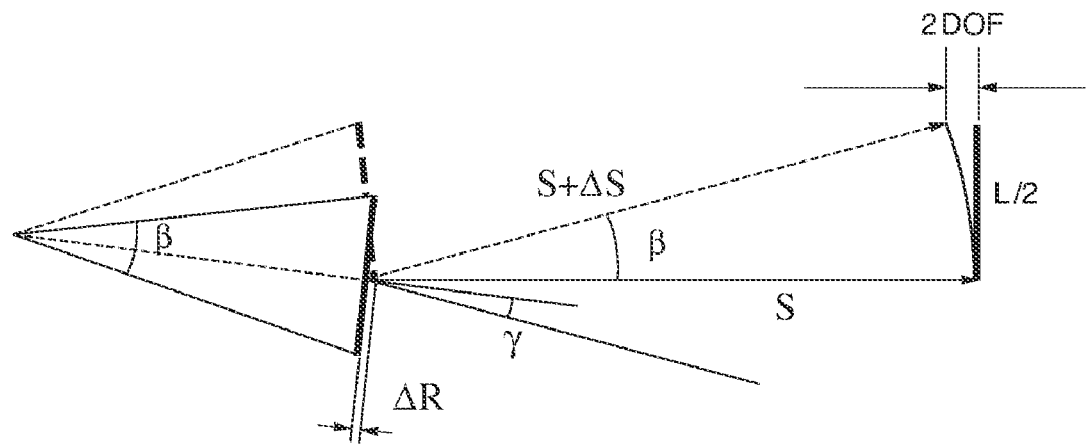
FIG. 14c is a schematic diagram of the scanning geometry of an embodiment of the polygon of FIG. 14.

Referring also to FIG. 14c, additional parameters can be derived, such as the scanning radius (S), which is given by:

$$S = L/(2 \tan \beta) \qquad (10)$$

As a polygon is not round, the distance between the polygon and an image surface is different for the central and border points of the facet. That is, the distance for the facet edge is longer by .DELTA.S. The change of polygon radius is given by:

$$\Delta R = D/2(1/\cos(\beta/2) - 1) \qquad (11)$$

Thus the increase of the scanning radius is given by:

$$\Delta S = 2 \Delta R \cos \gamma = D \cos \gamma (1/\cos(\beta/2) - 1) \qquad (12)$$

The sag of the focal surface is twice the depth of focus (DOF):

$$2\text{DOF} = S(1 - \cos \beta) - \Delta S \cos \beta \qquad (13)$$

Thus the change of distance along the beam, which should be within the allowable defocus, is given by:

$$2\text{DOF}/\cos \beta = S(1/\cos \beta - 1) - D \cos \gamma (1/\cos(\beta/2) - 1) \qquad (14)$$

Figure 14D:
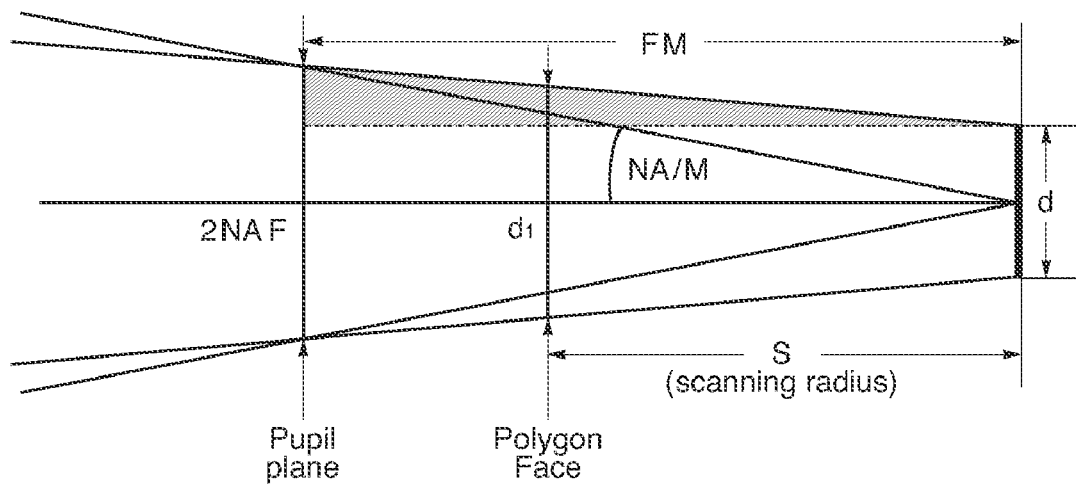

FIG. 14d is a detailed fragment of FIG. 14a. This is used to determine the required focal length (F) of the scanner. From similarity of the shaded triangles:

$$\frac{(d_1 - d)/2}{F \times NA - d/2} = \frac{S}{F \times M} \qquad (15)$$

Evaluating F:

$$F = \frac{S \times d}{2S \times NA - M(d_1 - d)} \qquad (16)$$

The rotational speed of polygon (v) is determined by linear scanning speed of spot V derived from equation (5):

$$v = V/(4\pi S) \qquad (17)$$

Figure 15:
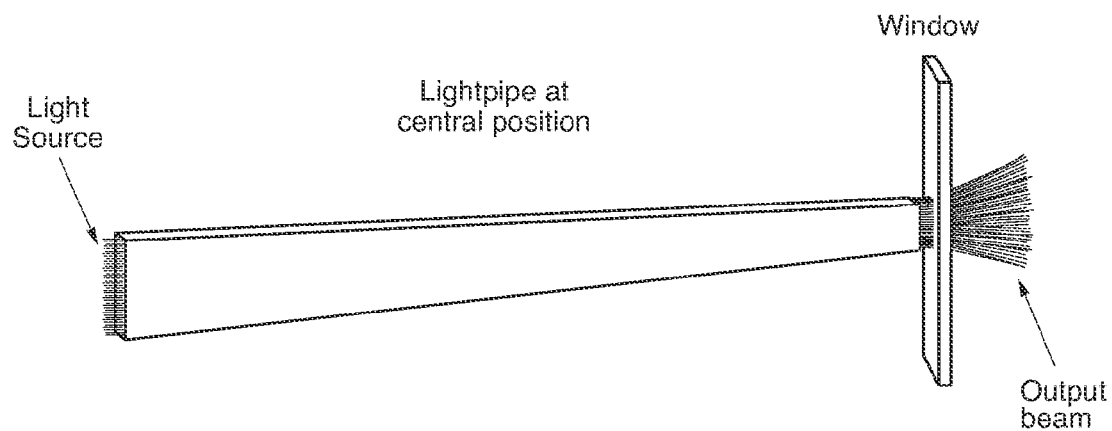
FIG. 15 and FIG. 16 are exemplary general 3D views of an optical system according to an embodiment of the disclosed technology.
Figure 16:
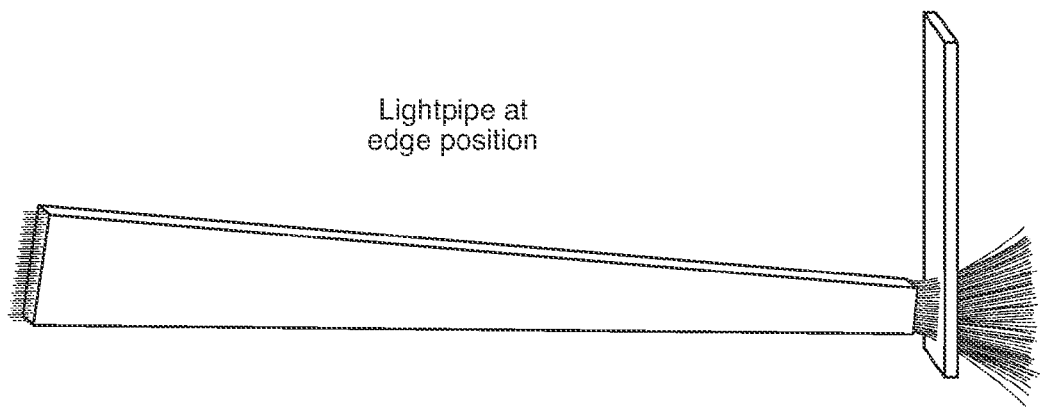

In one illustrative embodiment, the acquiring of the light emitted by the source, the shaping of the output beam, and its scanning is provided by a single optical element. FIG. 15 and FIG. 16 show the general view of the optical system according to this embodiment of the disclosed technology.

The optical element exhibits flat surfaces and does not have an optical power. Its input face is positioned close to the light source or to its image provided by additional optical system (not shown in the drawings). The dimensions of the input face are made large enough to preferably acquire most, if not all, of the complete beam produced by the light source. The acquired light is guided through the element to its output face by total internal reflection (TIR) from the side faces. Therefore, the optical element serves as a light pipe. An antireflection coating can be deposited on the input and output faces of the pipe to reduce the Fresnel losses due to reflection from these faces. The dimensions and shape of the output face determine the profile of the output beam. The same factors along with the pipe length affect the divergence of the output beam.

Further, FIG. 15 and FIG. 16 show a light source, a lightpipe, and an output window covering an orifice of the system enclosure. When the lightpipe is tilted related to the axis of the light source, the output spot on the window is shifted from the central position. The movement of the lightpipe can be achieved, for example, by its mounting on a rocker, which provides the rotation about the axis positioned close to or coincided with the entrance lightpipe face. If this axis is located far from the mentioned position, the required size of the input face becomes larger. In this case, the available range of the output beam parameters is more limited from the bottom as the amount of input BPP is increased. The same change should be made with the amount of output BPP that is the product of output face size and sine of divergence angle for the output beam.

The supports of lightpipe, when its outer sides serve as working surfaces, should preferably be made from metal and provide a small contact area. Any type of external contact destroys TIR conditions on the side faces and affects the light propagation inside the lightpipe. However, the use of metal holders provides much lower attenuation of the light than the use of dielectric supports. This can be explained by the following consideration. When TIR is disturbed by dielectric, the rays meeting the disturbed area almost completely leave the pipe penetrating into the contacted dielectric. When contact with metal disturbs TIR, the significant part of power is reflected back to the pipe as is typical in reflections from metal.

The following analytical approach has been developed to connect the parameters of input and output beams of the lightpipe. It allows making a design of the pipe based on the required amounts of these parameters.

Figure 17:
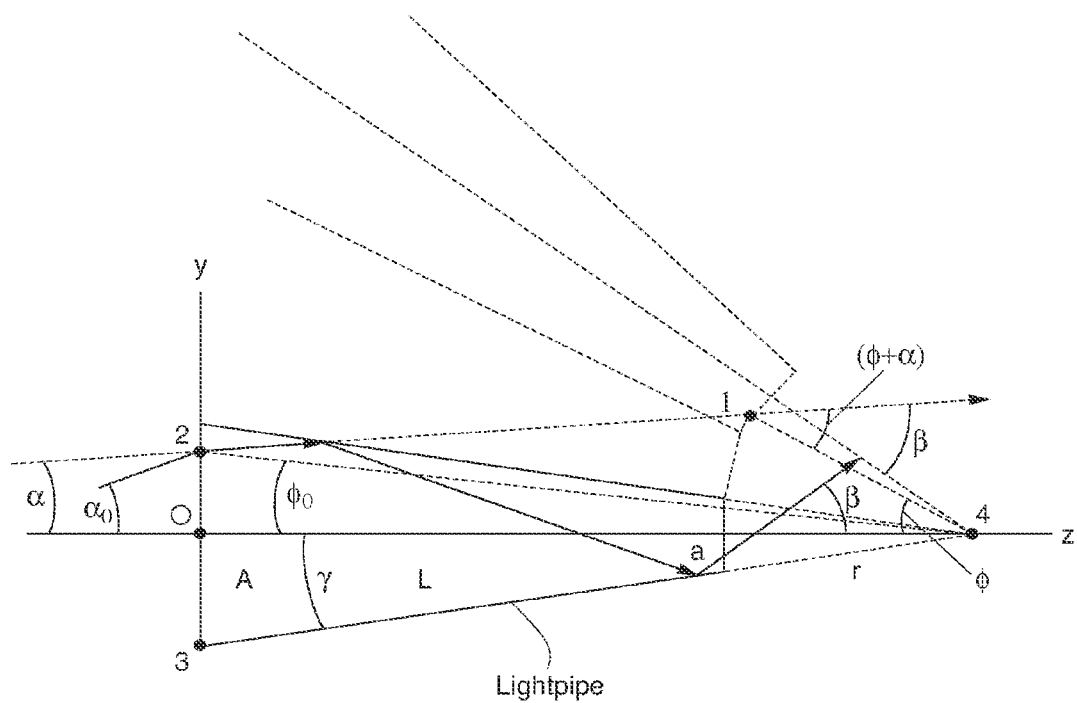
FIG. 17 and FIG. 18 illustrate an analytical approach to the design of an illustrative light pipe.

FIG. 17 shows the geometry of the light pipe. A and a are the dimensions of its input and output windows, and L is its length. The material of the pipe has a refractive index n. Pipe is tapered to the output face with angle γ to the axis, which is determined by the lightpipe parameters as:

$$\text{Tan } \gamma = (A-a)/(2L) \tag{18}$$

The ray entering the pipe at the distance y from its axis OZ has the internal angle of incidence α. The external incident angle $\alpha_0$ is determined by Snell's law:

$$\text{Sin } \alpha_0 = n \text{ Sin } \alpha$$

After several reflections from the side faces, which are tilted to the axis at angle γ, the ray leaves the pipe at larger internal angle β to the axis. After each reflection, the absolute value of the tilt angle is increased by the amount of 2γ. It is convenient to use the unfolded ray path drawn by dotted line. The ray propagation in the lightpipe can be readily described with polar coordinate system having a center at point 4. The starting point has polar coordinates $\{r+L, \phi_0\}$, the end point $-\{r, \phi\}$. In the triangle 124, the angle at the corner 2 is equal to $(\phi_0+a)$, at the corner 4 it is equal to $(\phi-\phi_0)$. Therefore, the amount of angle that is external to this triangle is equal to $(\phi+a)$. This angle is shown in the drawing. From the triangle 124:

$$\frac{r}{\text{Sin}(\alpha+\phi_0)} = \frac{r+L}{\text{Sin}(\pi-\alpha-\phi)} = \frac{r+L}{\text{Sin}(\alpha+\phi)}$$

From the triangle O34:

$$\frac{r}{r+L} = \frac{a}{A}$$

Combining the two last equations, one can obtain the expression:

$$A \text{ Sin}(\alpha+\phi_0) = a \text{ Sin}(\alpha+\phi) \tag{19}$$

The amount of $\phi_0$ depends, on the distance from axis y as $$\text{Tan } \phi_0 = (2y/A)\text{Tan } \gamma \tag{20}$$

As can be seen from FIG. 17, the amount of output angle β is close to $(\alpha+\phi)$. The difference between them is always less than tapering angle γ, which is usually small related to the output angle. On the contrary, the amount of $\phi_0$ on the left side of equation (19), which is also less than γ, cannot be neglected compared to α as being of the same order of magnitude. For these reasons, equation (19) can be used for a good estimation of output angle β for arbitrary ray:

$$\text{Sin } \beta \approx (A/a)\text{Sin}(\alpha+\phi_0) \tag{21}$$

The system of equations (18)-(21) allows the rough tracing of arbitrary ray inside the lightpipe.

The largest output angle corresponds to the extreme ray, which has a maximal input angle $\alpha_{max}$ and enters the pipe at the edge of input face, so that $\phi_0 = \gamma$. Tracing this ray gives the estimation of the numerical aperture of output beam $NA_{out}$:

$$NA_{out} = n \text{ Sin } \beta_{max} \approx n \text{ Sin}(\alpha_{max}+\phi_{max}) = n(A/a)\text{Sin}(\alpha_{max}+\gamma) \tag{22}$$

$$NA_{in} = \text{Sin } \alpha_0^{max} = n \text{ Sin } \alpha_{max}. \tag{23}$$

The amount of $\alpha_0^{max}$ in (23) is determined by the light source divergence and by the magnitude of angular lightpipe oscillation, which provides the output beam scanning.

Equation (22) shows that the amount of BPP is not conserved throughout the lightpipe. If it were so, $\text{Sin}(\alpha_{max}+\gamma)$ would be replaced with $\text{Sin } \alpha_{max}$ The derived equations can be applied to an extending pipe also. In this case, A<a, γ<0, and $NA_{out} < NA_{in}$ The system of equations (18), (22), (23) gives an approximate but close to the correct connection between lightpipe parameters and numerical apertures of input and output beams. Therefore, they can be used for the preliminary design of a lightpipe. Usually $NA_{in}$ and A are given due to the chosen light source and the selected angular magnitude of lightpipe movement. $NA_{out}$ and a are also determined by the application of scanner. The length of pipe and/or its material can be selected from the mentioned equation set.

From equations. (22) and (23):

$$\gamma = \text{Sin}^{-1}[(a/A)(NA_{out}/n)] - \text{Sin}^{-1}[NA_{in}/n] \tag{24}$$

Equation (18) is used to calculate the pipe length from the found value of γ.

$$L = (A-a)/(2 \text{ Tan } \gamma) \tag{25}$$

As was mentioned above, the direction of ray becomes steeper related to the pipe axis during the propagation. As a result, its incident angle i to the pipe side surface becomes smaller. At the end of pipe this angle may become lower than TIR angle, which is determined by refractive index n of material as $\text{Sin}^{-1}(1/n)$. Under this condition, the ray leaves the pipe and is lost for the delivered light. To avoid the power losses in the light pipe, its tapering angle should be top limited by some amount, which is determined below.

Figure 18:
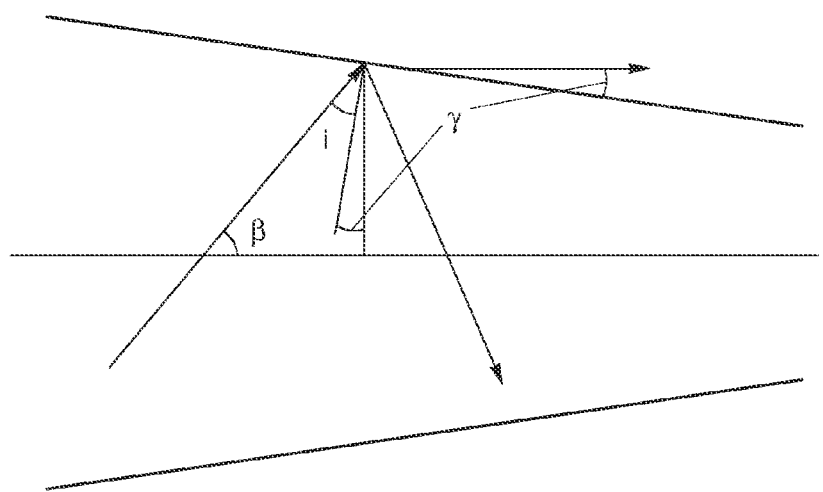

One can see in FIG. 18 that the tilt angle of the ray β, its incident angle to the pipe side i, and the angle of pipe tapering γ are connected as follows:

$$i+\gamma=90°-\beta \tag{26}$$

Let's apply this equation to the critical conditions at the end of pipe, when angle i is equal to minimal TIR angle for the reflection from the pipe side surface, and β corresponds to the required output numerical aperture $NA_{out}$. In this case, $$\text{Sin } i = 1/n; \text{ Sin } \beta = NA_{out}/n \tag{27}$$

and equation (26) gives the top limit $\gamma_o$ for the amount of light pipe tapering angle:

$$\gamma < \gamma_o = \text{Cos}^{-1}(NA_{out}/n) - \text{Sin}^{-1}(1/n) \tag{28}$$

The amount of γ calculated from Eq. (24) for the specific set of parameters $\{NA_{out}, A, NA_{in}, a\}$ should be compared with $\gamma_o$ determined by Eq. (28). If $\gamma > \gamma_o$ the required parameter set cannot be provided by any lightpipe without power losses. To avoid the losses, the set should be modified.

The design of the lightpipe can be finalized on the basis of the exact ray tracing. The equations that describe the correct dependence of output angle on other parameters are not as straightforward as those derived before.

The value of angle between the ray and the pipe axis is changed by 2γ at each reflection from the side. Therefore, the output internal angle depends on number of reflections inside the pipe N as:

$$\beta = \alpha + 2\gamma N[\alpha/\text{Abs}(\alpha)] \quad (29)$$

Here Abs( ) stands for the absolute value and is included to consider any sign of α and γ. Taking into account the change of angle sign at each reflection, the real amount of output angle is:

$$\beta = (-1)^N(\alpha + 2\gamma N[\alpha/\text{Abs}(\alpha)]) \quad (30)$$

The number of reflections N for an arbitrary ray is determined by its final angular coordinate φ shown in FIG. 17. One can see in this drawing that reflection happens when the current angular ray coordinate becomes equal to each of the following amounts:

$$\phi_N = \pm(2N-1)\text{Abs}(\gamma)$$

For this reason, the N value is equal to:

$$N = \text{Int}\{\text{Abs}[(\phi+\gamma)/(2\gamma)]\} \quad (31)$$

Here Int{ } means the integer part of the indicated ratio. The amount of φ is calculated from Eqs. (18)-(20).

The system of equations (18)-(20), (30), (31) allows exact tracing of arbitrary ray inside the lightpipe. The solution for the extreme ray with parameters: $\alpha = \text{Sin}^{-1}(NA_{in}/n)$; $\phi_0 = \gamma$ gives the dependence of output beam divergence $NA_{out}$ on lightpipe parameters and $NA_{in}$.

As against to the equation (24) in simplified analysis, the calculation of γ cannot be made directly from the exact equations. The optimal amount of γ and then the pipe length are determined from the position of local minimum of $NA_{out}$ in its dependence on γ. This will be illustrated in the embodiment described below.

Apart from the divergence of the output beam, its important parameters are the uniformity of irradiance at the pipe output and the shape of cross section. When irradiance profile is flat, the shape and dimensions of output beam just copies those of the pipe output face. The irradiance uniformity is achieved when the number of reflections experienced by light rays inside the pipe is enough large. Therefore, the analysis of N in equation (31) is an important part of the pipe design.

Figure 19:
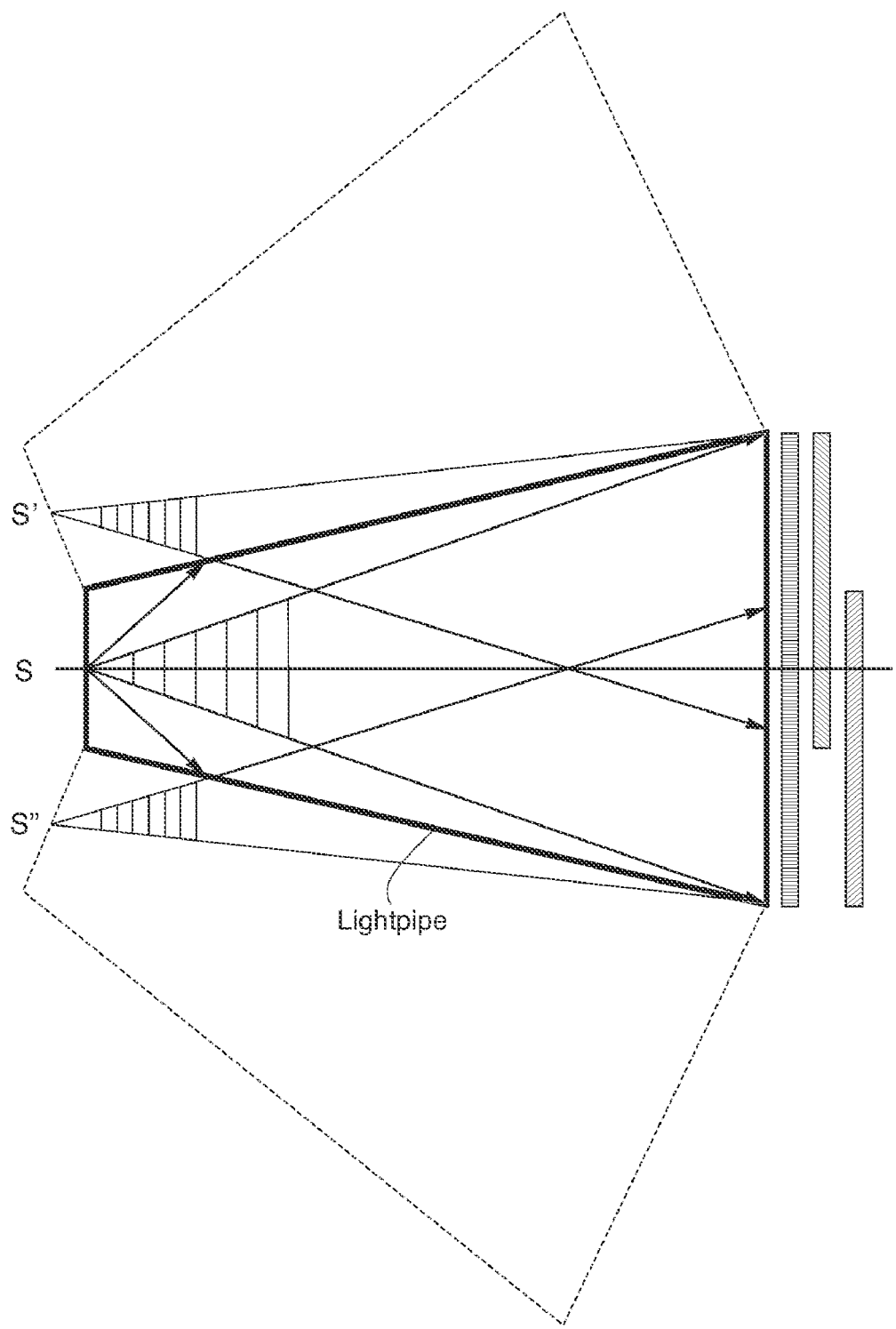
FIG. 19 shows the averaging of irradiance at the output of an illustrative light pipe.

FIG. 19 demonstrates the necessity of such reflections for the shaping of output spot.

Although the extending pipe is drawn in the FIG. 19, the same conclusion is correct for tapering pipe also. For illustrative purpose, only one emitting point S at the input face of lightpipe is drawn. One can see from the drawing that the light source is effectively multiplied because of ray reflection. For each reflection from the sides, one extra virtual source is generated. FIG. 19 shows that irradiance distribution on the output face is determined by the mixture of three section-lined beams. Because of that, the initial irradiance is homogenized due to this mixture and provides almost uniform distribution at the output. Two-three virtual sources on each side of the pipe are enough to make the output irradiance uniform. So the side rays should experience 2~3 sequential reflections inside the pipe.

Figure 20:
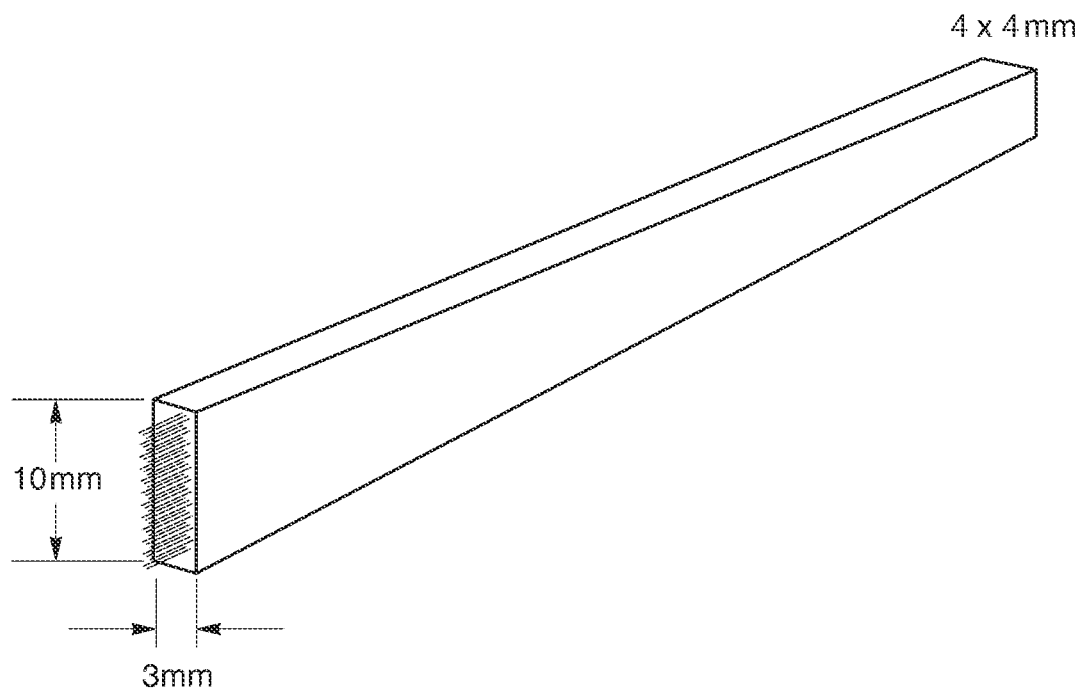
FIG. 20 is a close view of a light pipe for an embodiment of the optical system.

The optical system for coupling to laser bar, which is used as a light source, for forming a flat square spot on the output window, and for one-dimensional spot scanning has been designed in accordance to the disclosed method and was tested with computer simulations. A close view of the single optical element—lightpipe—is illustrated in FIG. 20.

In one illustrative embodiment, the lightpipe can be made from BK7 glass of the Schott catalog. The dimensions of its input face 10 mm×3 mm provide the complete collection of the light emitted by laser bar. The distance between bar and pipe is 1 mm, the gap between pipe and output window is the same. The pipe length is 80 mm. The angular magnitude of the pipe oscillation is 7° that provides 10 mm of the linear magnitude of spot on the window.

The length of the lightpipe can be selected to minimize the divergence of output beam, when dimensions of input and output faces, divergence of laser bar, and angular magnitude of pipe are given. The tapering vertical cross section of the pipe (10 mm->4 mm) was used for optimization.

Figure 21:
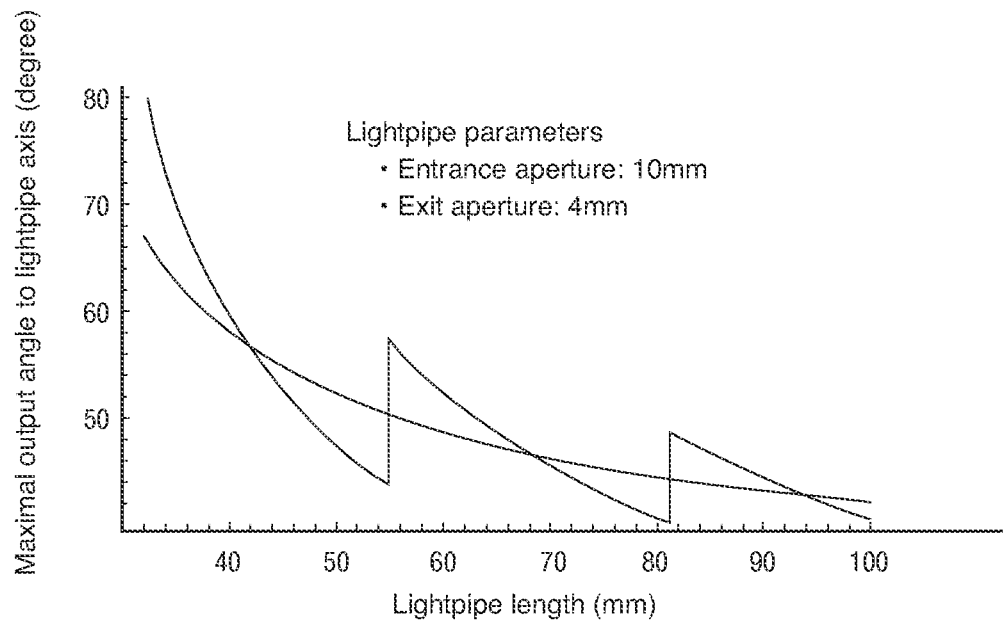
FIGS. 21-23 demonstrate the selection of an illustrative pipe length.

FIG. 21 shows the dependence of output angle for the extreme input ray on the pipe length, which is calculated from the approximate equation (22) and from the exact one (29). The absolute value of the output angle regarding the pipe axis is shown in FIG. 21.

Figure 22:
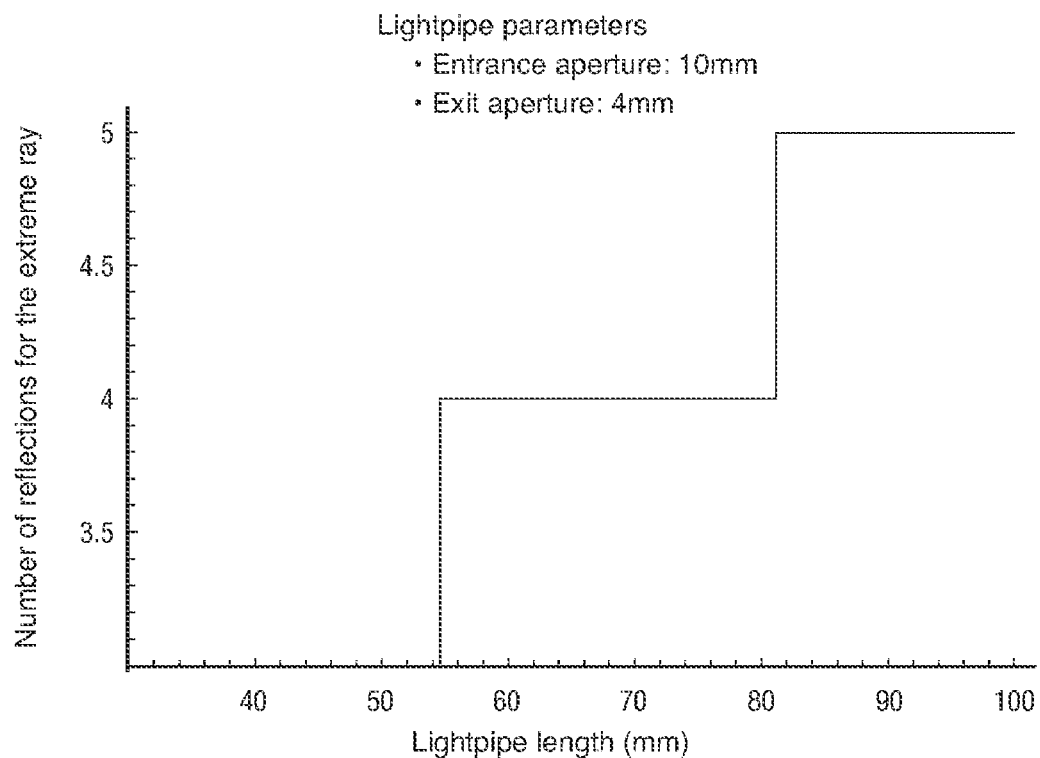

The number of reflections of the same extreme ray inside the pipe for various pipe length is shown in FIG. 22. The graph is calculated in accordance to equation (31).

One can see from FIG. 21 that the smooth curve corresponding to Eq. (22) actually provides the average amounts of the exact data from Eq. (29) displayed with the stepped curve. For this reason, the equations of the simplified analysis should be used for the preliminary design only.

To provide the most narrow output beam, the pipe length should be selected in the minimum of the correct stepped curve. There are two minima: about 55 mm and about 80 mm. Although the difference between them is not significant, the second one is preferable.

The reason is that for the tilted pipe the extreme ray should be located at the end of the interval with even number of reflections. When the pipe is tilted, the input angular distribution becomes asymmetrical, and the rays with maximal incident angles (extreme rays) exist on only one side of input aperture. This will also produce the asymmetry in the output angular distribution, as the extreme rays correspond to maximal output angle. Depending on the number of reflections for the extreme ray, the sign of its output angle is the same as for the input angle (N is even) or opposite (N is odd). The mentioned angles are measured regarding the pipe axis. It can be seen that when higher angles in the distribution have the same sign as at the input, the spot size on the window is smaller. Looking at FIG. 22, one can see that 80 mm minimum belongs to the end of four reflections interval, while 55 mm—to three reflections, therefore the first one is selected.

Figure 23:
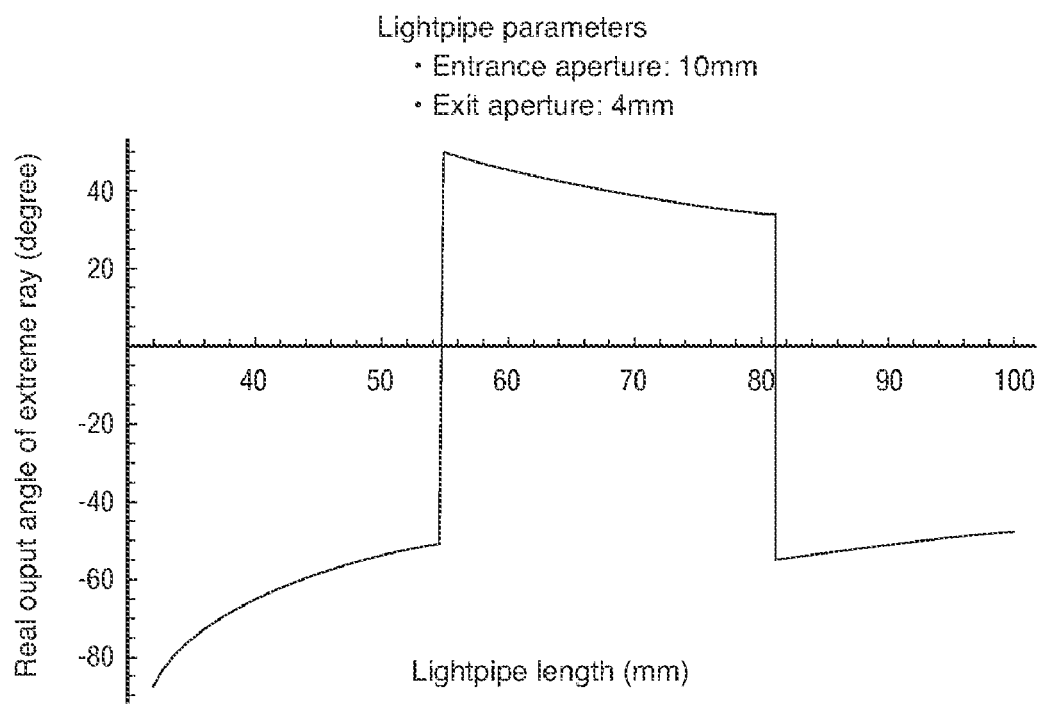

This conclusion is confirmed by FIG. 23, where the real signed amount of output angle according to Eq. (30) is displayed after the subtraction of 7° tilt angle. Therefore, FIG. 23 shows the output angle of the extreme ray regarding the perpendicular to the window, which determines the linear extension of spot.

In this graph, the difference between absolute values of output angles in minima at 80 mm and 55 mm becomes significant and equal to 17 degree. This clearly shows the advantage of selecting the first one to squeeze the spot on the window for the pipe edge position.

As the extreme ray is located at the end of interval of 4 reflections in FIG. 22, many rays with lower amounts of input parameters y<A/2, and $\phi_0 < \gamma$ will also experience 4 reflections from the sidewalls. This number is quite enough to provide the uniform output irradiance in the vertical direction for FIG. 20.

Figure 24:
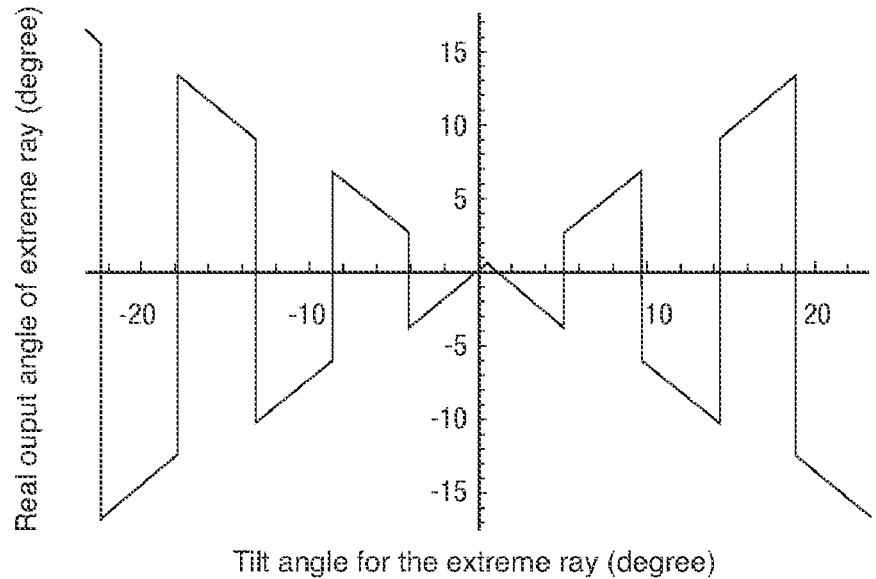
FIGS. 24, 25 show the study of pipe design in the widening section.

In the horizontal direction, the angular distribution is narrower, though the input divergence of the laser bar is larger in this direction. The reason is that the pipe is extending in horizontal cross section and is not tilted in this direction. FIG. 24 shows the dependence of output angle for the rays entering the pipe at y=1.5 mm on their input angle within the range of fast axis divergence of laser bar. The graph is calculated from Eq. (30).

Figure 25:
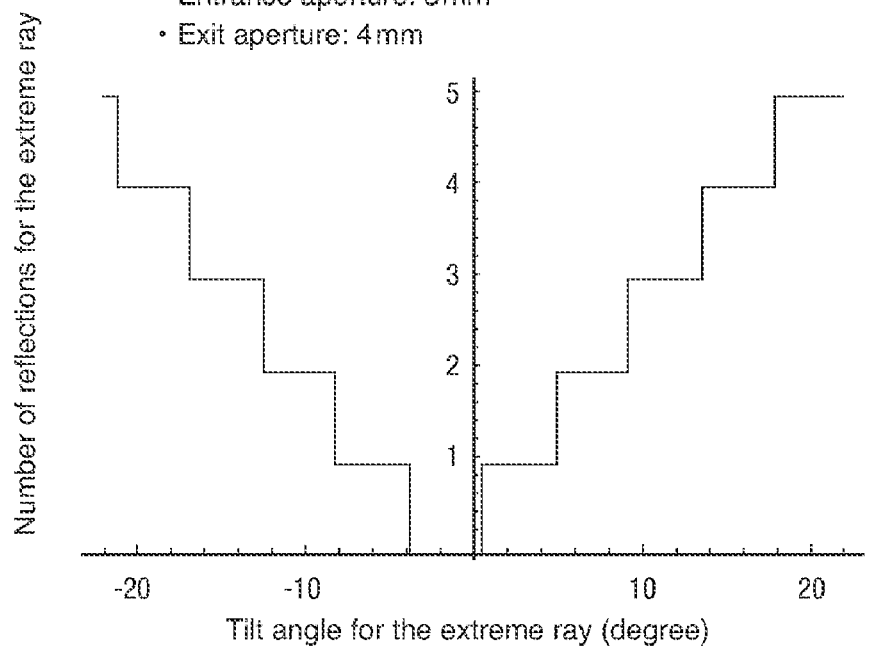

Number of reflections for the same rays is displayed in FIG. 25. The large value of N provides a good uniformity of output irradiance in horizontal direction as well as in the vertical one.

The system performance can be tested with ZEMAX software.

Figure 26:
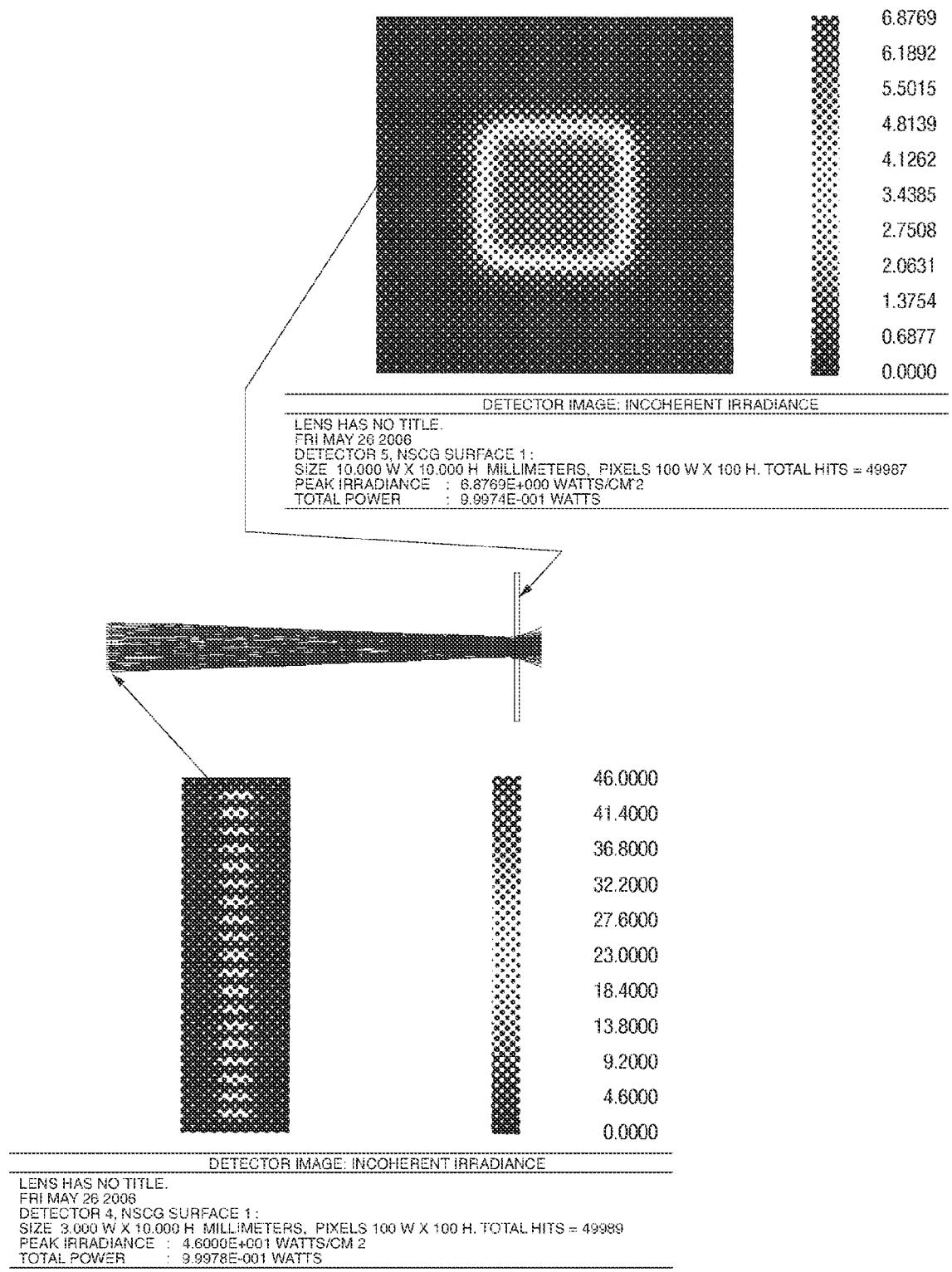
FIG. 26 shows the ray paths through the light pipe and irradiance distribution at the entrance and the exit of light pipe at the central position.

FIG. 26 summarizes the results of a system simulation for the central pipe position. It contains the ray traces through the system, and the irradiance at the input face of the lightpipe and on the output window. One can see highly non-uniform irradiance at the entrance with highlighted peaks from 19 emitters of the laser bar. After homogenizing by the lightpipe, the irradiance distribution on the window becomes almost flat.

Figure 27:
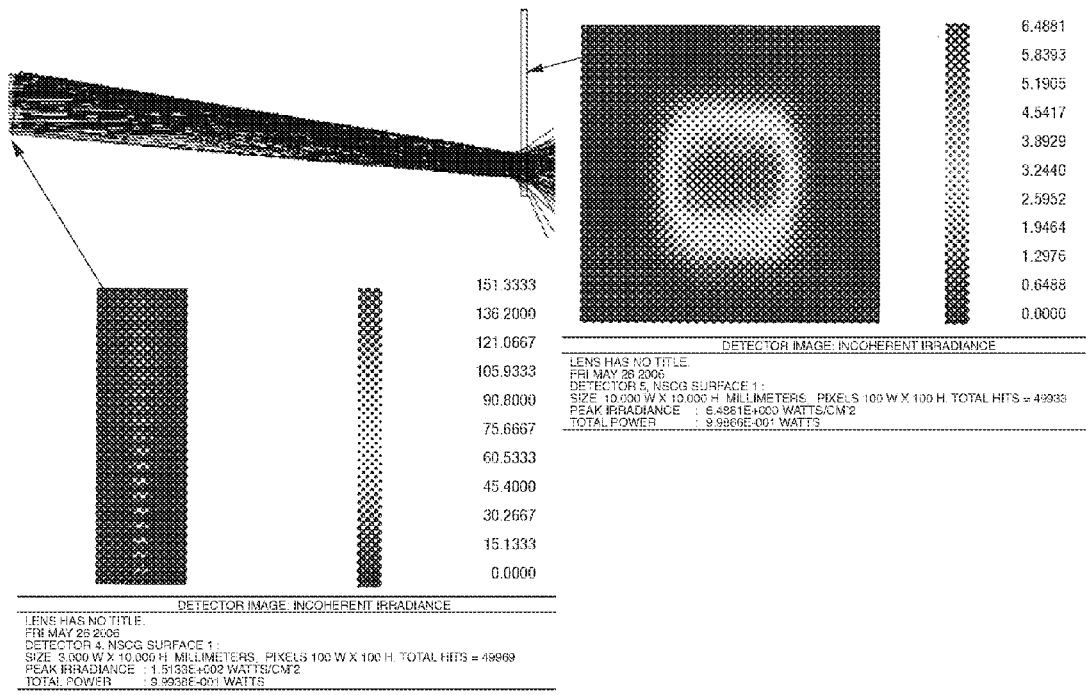
FIG. 27 shows the ray paths through the light pipe and irradiance distribution at the entrance and the exit of light pipe at the edge position.

FIG. 27 shows the same data for the pipe tilted by 7° to the central position. The output irradiance distribution is more diffused and less uniform than in FIG. 26 because of more than doubled maximal input angle and of increased distance to the window. Nevertheless, the spot shape is still close to square.

Figure 28:
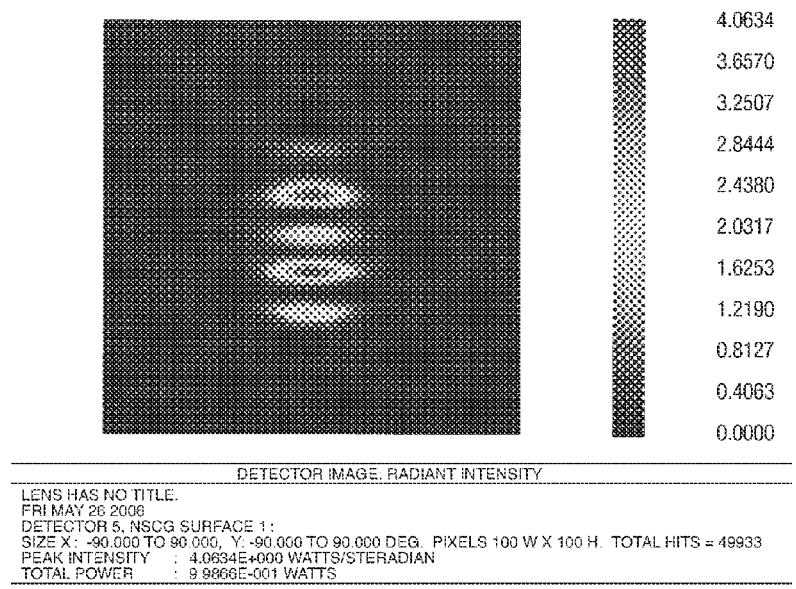
FIG. 28 gives the output distribution of radiant intensity for the edge light pipe position.

FIG. 28 shows the dependence of the power delivered under the conditions of FIG. 27 on the angle of incidence to the output window. The vertically arranged separate angular peaks are produced by the virtual light sources, which are generated by sequential reflections from the lightpipe sides, similar to the process described in FIG. 19. The vertical angular range is quite symmetrical, and covers ±35° that is close to the estimation from FIG. 23 for 80 mm pipe.

As a summary, the simulation results confirm the validity of the developed method of the pipe-based scanner design.

The lightpipe can be mounted on a rocker whose varying tilt provides the linear scanning of the output spot. The periodical variation of the rocker tilt can be achieved with several kinds of actuators. The preferred way is to convert the uniform rotation of motor axis into the desired rocker movement.

Figure 29:
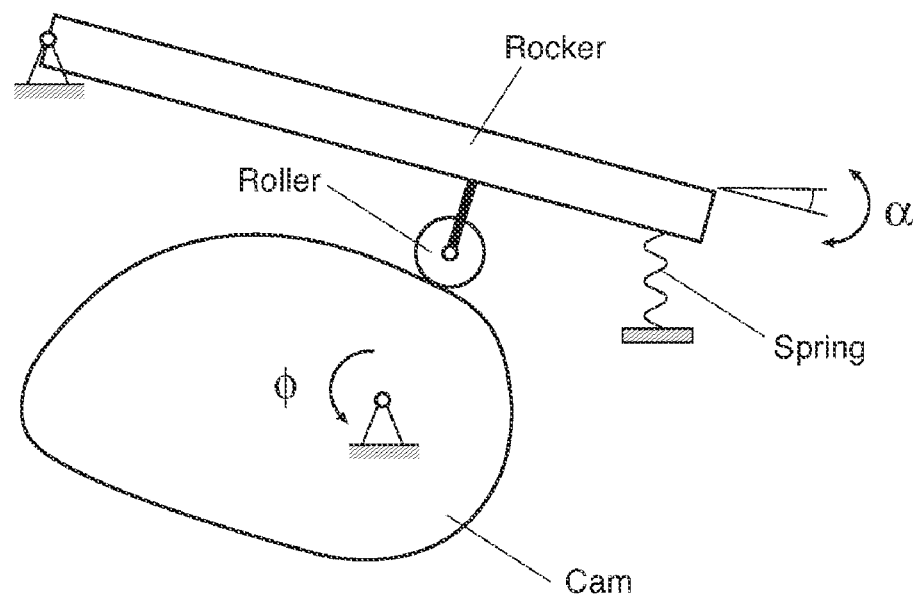
FIG. 29 illustrates an embodiment of a scanning mechanism based on a rotating cam.

FIG. 29 shows one embodiment of the scanner based on a rotating cam; a non-round cylinder eccentrically positioned on the motor axis. The cam mechanism provides the conversion of uniform motor rotation into angular reciprocation of rocker. The angular movement of rocker is determined by the cam profile and its rotational speed because cam and rocker are in permanent contact provided by roller and spring.

Depending on the cam shape, this mechanism can provide both unidirectional and bidirectional scanning of the output beam. Unidirectional scanning refers to the condition when the tilt angle of rocker a is increased for the most part of the rotational period of cam. After that, the rocker is quickly returned to the initial position. The ratio between working range of rotational angle θ of cam and the full 360° angle gives the amount of scanner duty cycle. When the shape of cam is symmetrical for the $1^{st}$ and $2^{nd}$ halves of rotational period, the scanning is bidirectional. In this case, the rocker tilt is increased and decreased for the equal parts of period.

Figure 30:
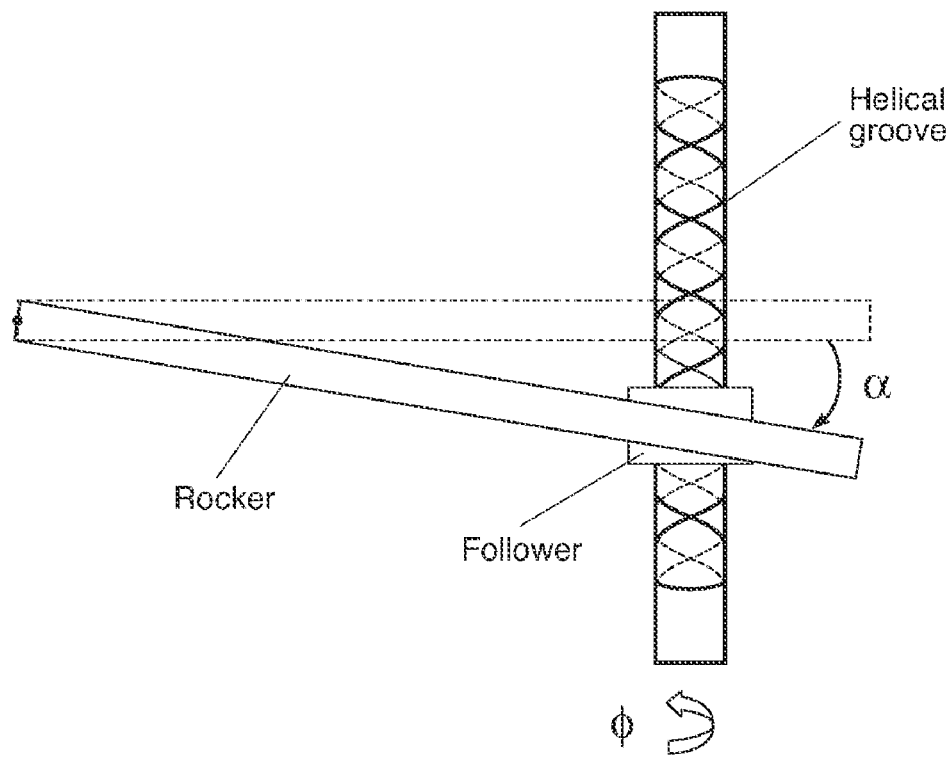
FIG. 30 shows an embodiment of a scanning mechanism based on a helical cam.

Another embodiment of the actuator is shown in FIG. 30. Two helical grooves are cut on the surface of shaft, which is rotated by motor (not shown in drawing). The directions of these spirals are opposite related to the shaft axis. The grooves are connected with each other at the shaft edges. One side of rocker is attached to the follower, which is driven by grooves during the shaft rotation. For the uniform rotation of shaft, the follower makes reciprocal movement along the shaft axis and provides the angular scanning of rocker.

Figure 31:
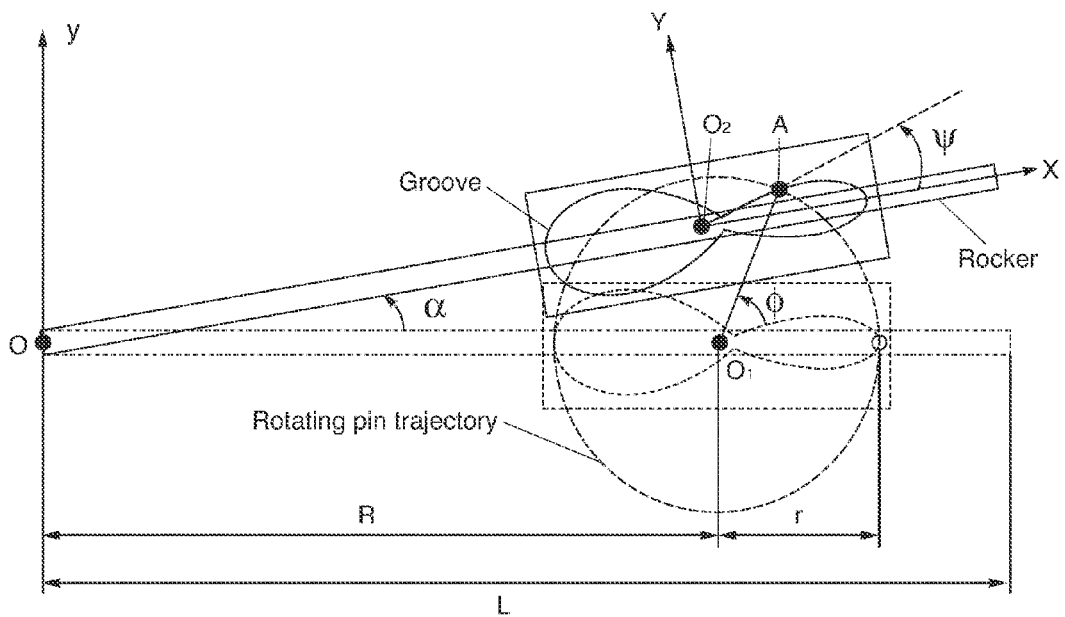
FIG. 31 shows an illustrative embodiment of a scanner containing a groove.

FIG. 31 shows the preferred scanner embodiment, which design will be described in detail below.

The actuator contains the plate, which is attached to the rocker, the groove of the specific shape made in said plate, and the pin positioned eccentrically on the rotor. The rotor is uniformly rotated by a motor (not shown), and said pin is positioned inside said groove so that it slides over the groove when rotated by the motor. The pivot point of the rocker is located in O. $O_1$ is the fixed center of the pin rotation, and the groove center is located in point $O_2$. A is the current point of contact between pin and groove. Pin is currently rotated by angle $\phi$, and rocker is tilted by angle $\alpha$. The groove shape will be calculated below in the moving coordinate system $XO_2Y$. The groove dimension along $O_2X$ is equal to the diameter of pin rotation 2 r. The center of groove coincides with center of pin rotation for the rocker middle position, when $\alpha=0$. The distance between rocker pivot point and groove center is R, and the rocker length is L.

Figure 32:
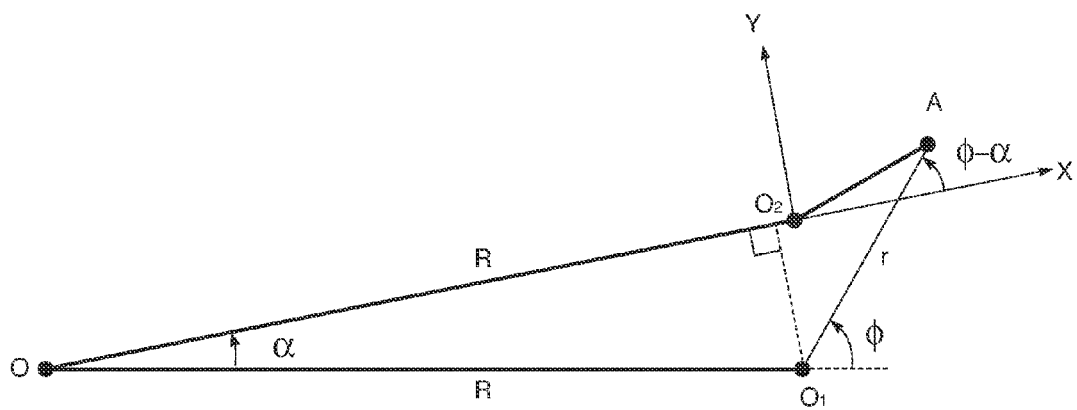
FIG. 32 illustrates an analytical approach to the design of the groove of FIG. 31.

The groove shape is precisely determined by its position R, by its length 2 r, and by the required angular movement of rocker, which can be expressed by the given dependence of $\alpha$ on $\phi$. The shape is calculated from the geometry shown in FIG. 32.

One can see that the coordinates of the point A, which is the current contact point between pin and groove, is determined for each angular position $\phi$ of pin by the following equations:

$$X(\phi)=r\cos(\phi-\alpha(\phi))-R(1-\cos(\alpha(\phi))) \quad (32)$$

$$Y(\phi)=r\sin(\phi-\alpha(\phi))-R\sin(\alpha(\phi)) \quad (33)$$

Varying the amount of $\phi$ in these equations, one can find the coordinates of all the groove points that determine the complete groove shape.

The function $\alpha(\phi)$ included in the equations is determined by the desired angular movement of rocker. As rotation angle $\phi$ is proportional to time for the uniform rotation, the dependence of tilt angle $\alpha$ on time will be the same as $\alpha(\phi)$.

Figure 33:
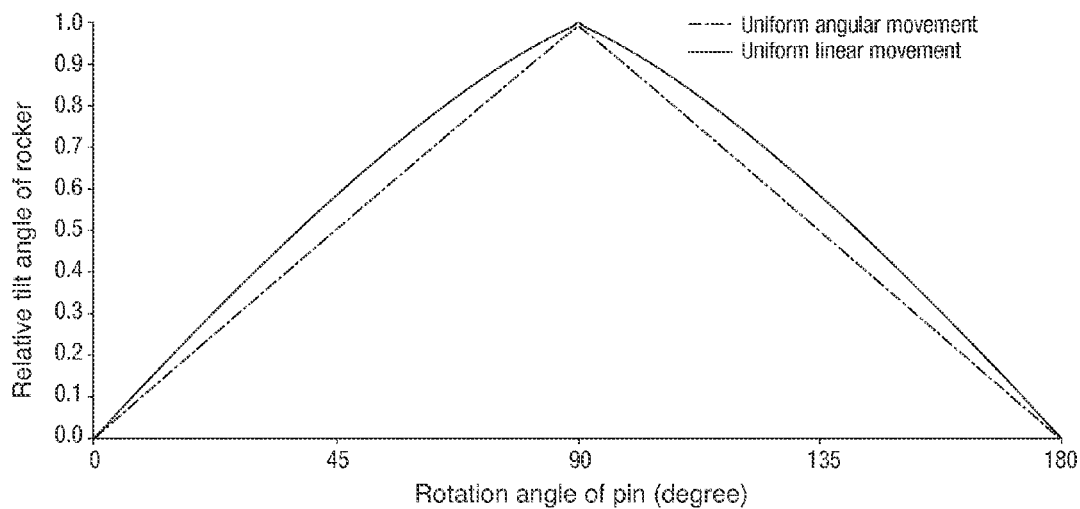
FIG. 33 demonstrates the relationship between motor rotation angle and rocker tilt angle for uniform angular movement of a rocker and uniform linear movement of a laser spot.

FIG. 33 shows this function for two the simplest and the most frequent angular movement used in scanning. The dashed curve corresponds to the uniform angular movement of rocker with the return points at quarter of total pin revolution. Actually, the point of return can be selected different. The solid curve provides the uniform linear movement of the light spot on the output window. In this case, the function $\tan(\alpha)$ should be changed in direct proportion to $\phi$, not $\alpha$ itself.

Figure 34:
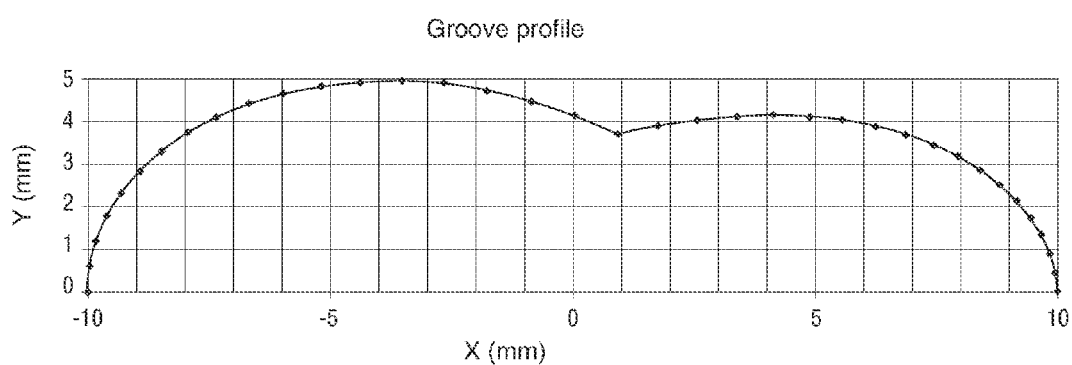
FIG. 34 shows the profile of a groove for specific input parameters.

FIG. 34 demonstrates the groove shape for specific scanner embodiment. The following amounts of parameters can be selected.

Radius of pin rotation: r=10 mm
Distance between rocker pivot point and groove center: R=45 mm
Maximal tilt angle of rocker: $\alpha_{max}=8°$
Uniform linear movement of the light spot (solid curve in FIG. 33)

The points shown in FIG. 34 correspond to the rotation angle variation with 5° step.

The drawn graph corresponds to the half of the full pin revolution: from 0° to 180°. When the same movement but in opposite direction is required for the $2^{nd}$ half period, the shape of the rest part of the groove will be symmetrical to the drawn one. In general, the movement of rocker from the middle point to another side can be provided different.

For the implementation of the disclosed scanning method, the groove should be cut in the plate of low-friction material, such as Teflon. The width of groove should be at least equal to the pin diameter. The theoretical curve in FIG. 34 has a kink point at ϕ=90°. In practice, the curve should be smoothed about this point with a curvature radius not below the pin diameter. Otherwise, the pin will be stuck at this point. This modification just slightly reduces the duty cycle of scanning from theoretical amount of 100%.

The proposed method of angular scanning provides the precise movement by very compact actuator. As shown in FIG. 34, the groove size 10 mm×20 mm is enough to meet the scanning requirements, which were tested above optically.

In one illustrative embodiment, the disclosed system can include an optical fiber. In such an embodiment, a key issue for the design of light delivery system is the comparison of optical invariants (BPP) of the light source and of the lightguide used in the system. If the amount for the latter is lower, there is no way to make the efficient coupling of the light source within the frame of simple optical solutions. BPP of some light source of interest can reach some units of mm that is much higher than acceptance BPP of conventional optical fiber. Therefore, an important consideration of the disclosed technology is a new kind of fiber, which acceptance BPP can be made as high as for say, laser bar along slow axis.

The increase of BPP for the proposed fiber is made through the raise of both contributing parameters: diameter and numerical aperture (NA).

The increase of fiber diameter from common fractions of millimeter to some millimeters can be applied to plastic fibers only; the glass fiber of such diameter would not be flexible. The application of plastic optical fibers (mainly made from PMMA) is now limited by visible spectral range because of high absorption in other regions. Even in visible area, the absorption of their materials is much higher than of a glass that limits the distance of light delivery. Recently developed perfluorinated polymers, such as Cytop by Asahi Glass or Teflon AF by DuPont can be successfully used for the light delivery, as they are transparent up to 1300 nm of wavelength.

Conventional optical fibers are made from two materials with different refractive indices: core should be more optically dense than cladding layer. The acceptance $NA_{fib}$ of fiber is determined by refractive indices as following:

$$NA_{fib} = (n_{core}^2 - n_{clad}^2)^{0.5}$$

Because of a small difference between $n_{core}$ and $n_{clad}$, the amount of $NA_{fib}$ is usually less than 0.5. This value can be almost doubled if fiber does not contain the cladding layer, as $n_{clad}$ in this case is replaced by 1 in the equation. A bare fiber made from Cytop or Teflon AF has an accepted numerical aperture of 0.9 corresponding to the refractive index 1.35 of these materials. The protection of fiber side surface from external contacts, which may destroy TIR conditions for the delivered light, is provided by flexible metal sheath like a gooseneck. This issue will be discussed later.

As an example, the amount of BPP for bare uncladded Cytop fiber with 2 mm of diameter would be equal to 1.8 mm that is higher than $BPP_s$ of laser bar along slow axis (1.7 mm). Therefore, laser bar can be easily coupled to such fiber without currently used redistribution between $BPP_s$ and $BPP_f$.

The coupling of extended source to the proposed fiber is made by single element of so-called flat optics, which does not have an optical power. This way is preferred to the use of lens because of cheaper manufacturing and of less sensitivity to the relative lateral shift.

Figure 35:
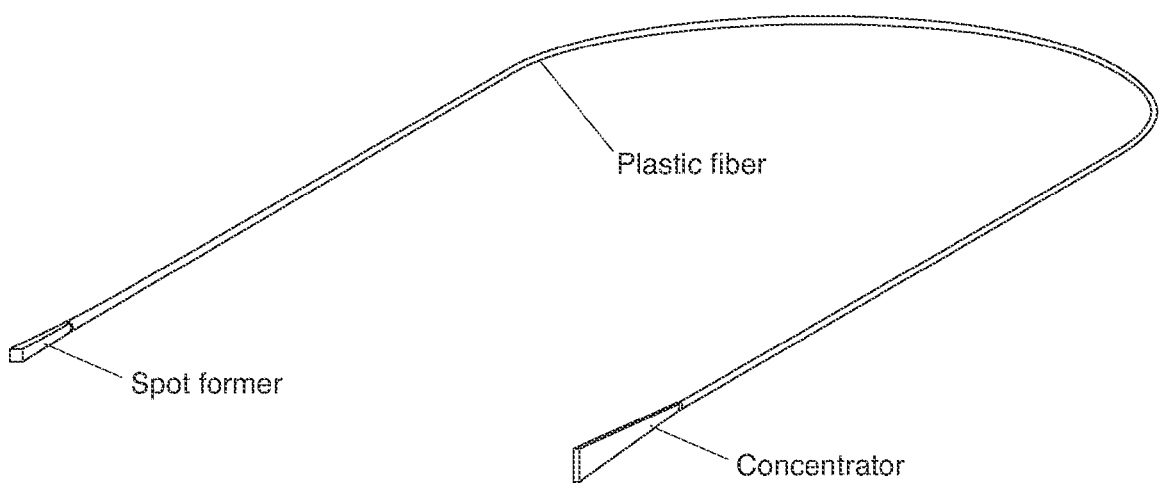
FIG. 35 is an exemplary general 3D view of an illustrative optical system.
Figure 36:
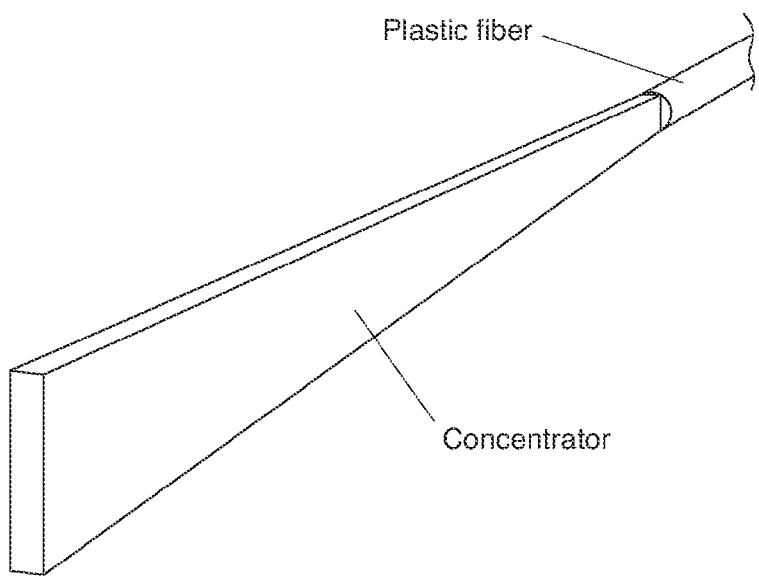
FIG. 36 and FIG. 37 show a close view of a concentrator and a spot former for an embodiment of the optical system of FIG. 35.
Figure 37:
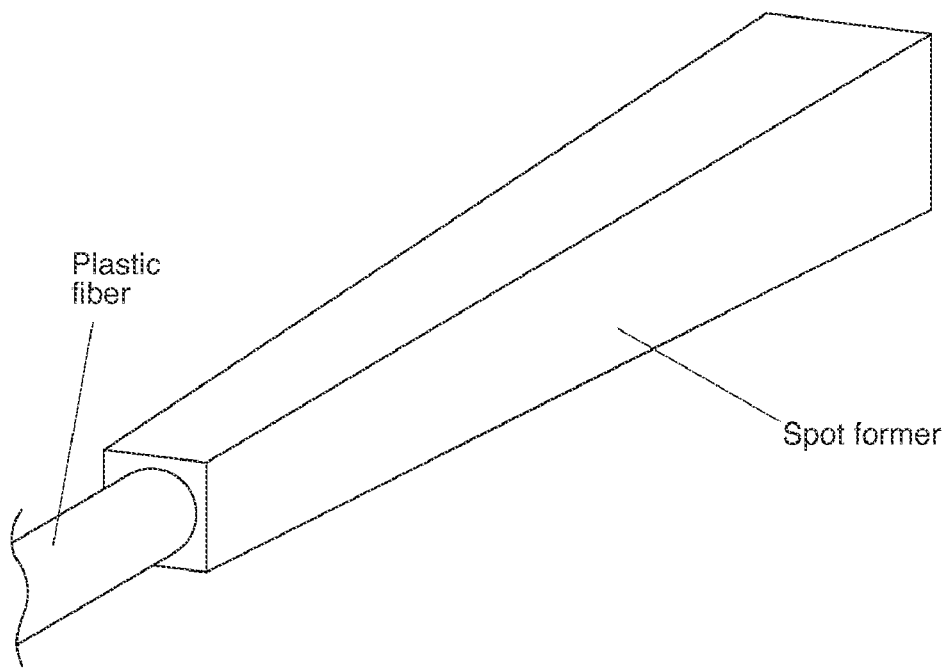

One embodiment of the disclosed technology uses the tapered rectangular light pipe as an optical concentrator, which reduces the size of the light source down to the fiber diameter. FIG. 35 shows the general view of the embodiment, FIG. 36 and FIG. 37—close view of Concentrator and Spot Former.

Figure 38:
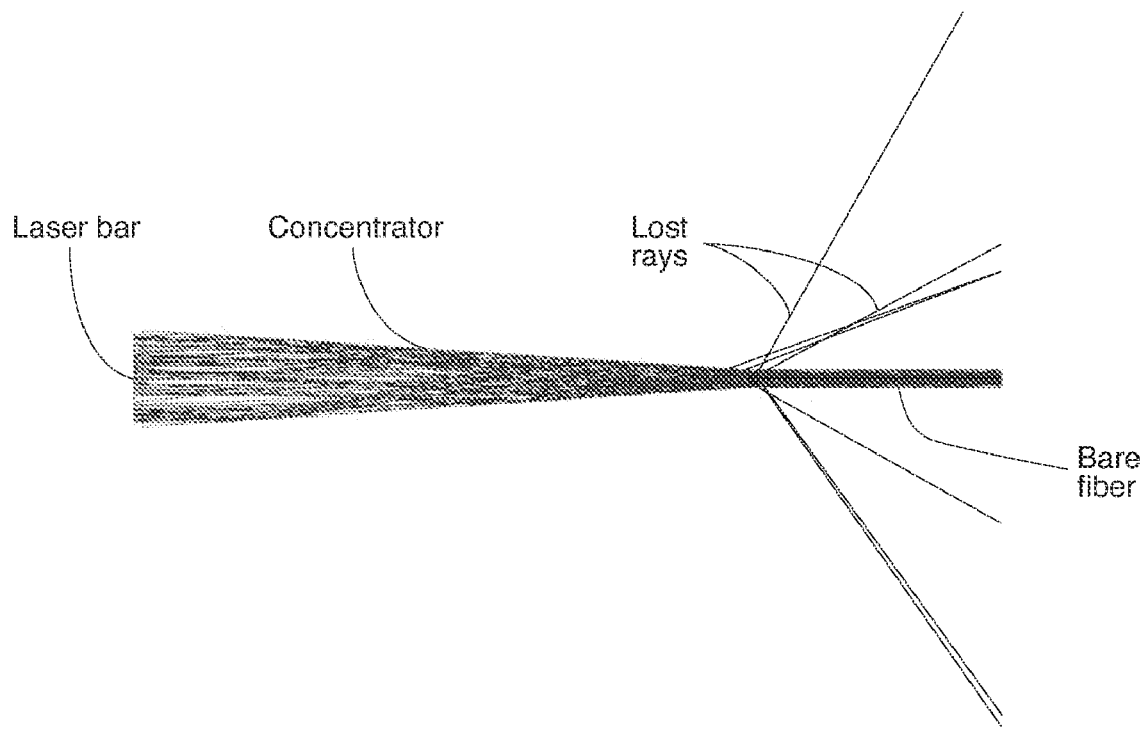
FIG. 38 is an illustrative view of light propagation from a light source through the concentrator to the fiber.

FIG. 38 demonstrates the simulation of light propagation from the light source through the concentrator to the fiber. As the number of lost rays is small compared to their total number, one can see that coupling efficiency is high. One can see that lost rays are located at the end of concentrator and at the beginning of fiber. The developed above theory of lightpipe design (Equations (18)-(31)) can be applied to the improvement of coupling efficiency. In this case, if $n_1$ is the refractive index of lightpipe material, Sin β should be replaced with $NA_{fib}/n_1$ in the mentioned equations.

Specifically, equation (28), which gives the top limit for the amount of light pipe tapering angle, is converted into:

$$\gamma < \gamma_o = \cos^{-1}(NA_{fib}/n_1) - \sin^{-1}(1/n_1) \quad (34)$$

If $NA_{fib}$ in the equation (34) is replaced by its expression through the fiber refractive index $n_2$, the equation can be rewritten in the form showing that material of the light pipe preferably should be more optically dense than material of the fiber.

$$NA_{fib} = (n_2^2 - 1)^{0.5}; \quad (35)$$

$$\sqrt{n_1^2 - 1} > \frac{\sqrt{n_2^2 - 1}}{\cos\gamma} + \tan\gamma$$

A concentrator can be made from any optical glass, as refractive indices of all of them are higher than of perfluorinated polymer—the fiber material. The optical connection between concentrator and fiber is made with optical epoxy or with adhesive cured by UV light.

The support of uncladded optical fiber, when its outer side serves as a working surface, is made by flexible metal sheath like a gooseneck. Any type of the external contact destroys TIR conditions on the fiber side and affects the light propagation inside the fiber. As was discovered by computer simulation of the disclosed optical system, the use of metal holders provides much lower attenuation of the light than the use of dielectric supports. The contacts between aluminum and fiber side occupying 0.5% of the total surface introduce only 0.04 dB/m of additional light attenuation. If the same fraction of fiber side surface is occupied by contacts with dielectric, the additional attenuation is tens times higher. This phenomenon can be explained by the following consideration. When TIR is disturbed by dielectric, the rays meeting the disturbed area almost completely leave the fiber penetrating into the contacted dielectric. When contact with metal disturbs TIR, the significant part of power is reflected back to the fiber as always happens for the reflection from metal. The experiments conducted with glass rods and bare plastic fibers positioned without any additional mechanical support inside the steel gooseneck did not reveal the increase of light attenuation delivered through the covered lightguides. That means the total contact area between the lightguide and surrounding gooseneck was not much larger than 0.5% used in the simulation.

The profile of the output beam at the opposite end of fiber is formed by another light pipe, either bonded to the fiber with optical adhesive or made from the same plastic material together with fiber. This combined fiber-pipe shape can be provided by injection molding process.

The output beam divergence is determined again by the amount of BPP of the coupled beam and by the exit size of the spot former. The cross section of the delivered beam copies the shape and dimension of the spot former cross section at the output. These conditions are provided by the enough large number of light reflections from the pipe sides as shown in FIG. 19

The optical system for coupling of laser bar was designed in accordance to the disclosed method and was tested with experiments and computer simulations.

The concentrator and the spot former are made from F2 glass of Schott glass catalog. Fiber of 1 m length and of 2 mm diameter is made from Cytop and bonded to both light pipes by UV-cured optical adhesive. Concentrator has a length of 70 mm, input face of 11 mm×1.8 mm, and output face of 1.8 mm×0.9 mm. The output rectangle is selected to be inscribed into 2-mm circle and to have larger dimension along the slow axis of the coupled laser bar. Laser bar is positioned at 1 mm from the input face of concentrator. The spot former is of 35 mm length, has 2.5 mm×2.5 mm input face, and 4 mm×4 mm output face. 3-dimensional drawings of the system and its elements are presented in FIG. 35-FIG. 37.

Figure 39:
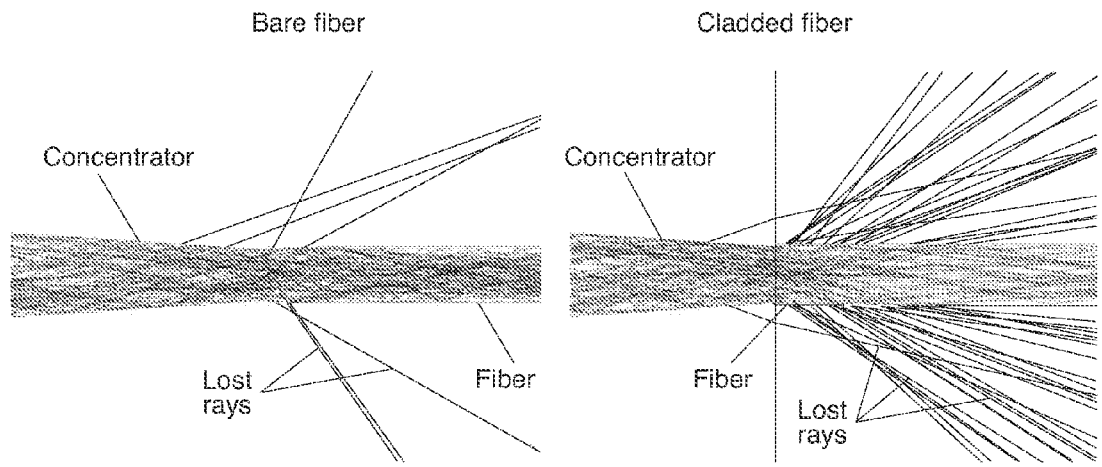
FIG. 39 demonstrates the advantage of uncladded fiber in the system of FIG. 35.

The system performance has been tested with ZEMAX software. FIG. 39 demonstrates the advantage of bare fiber compared to the use of the cladded fiber of the same core diameter but with acceptance $NA_{fib}=0.44$. One can see that more than 50% of the light collected by concentrator is not acquired by this fiber.

Figure 40:
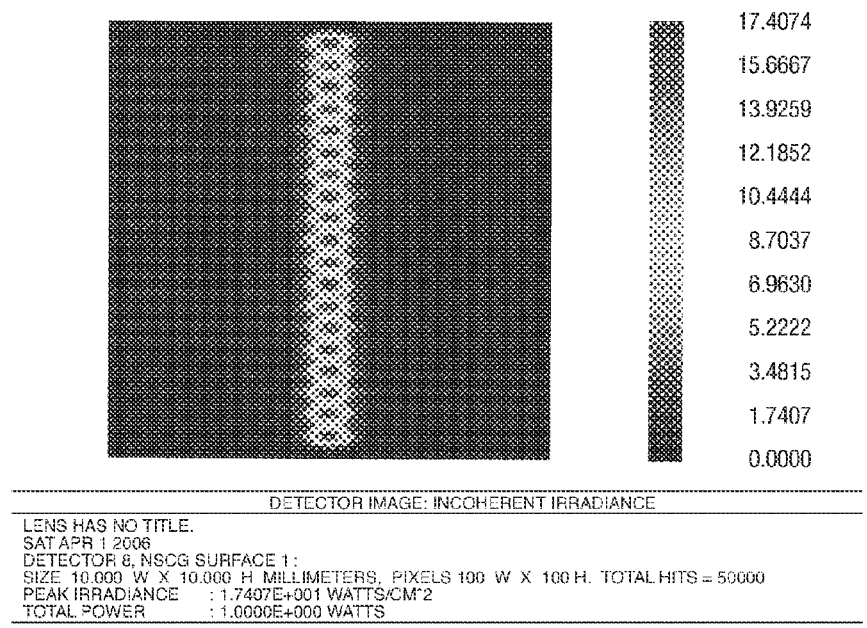
FIG. 40 and FIG. 41 show the irradiance distribution at the input and output of the concentrator for a disclosed embodiment.
Figure 41:
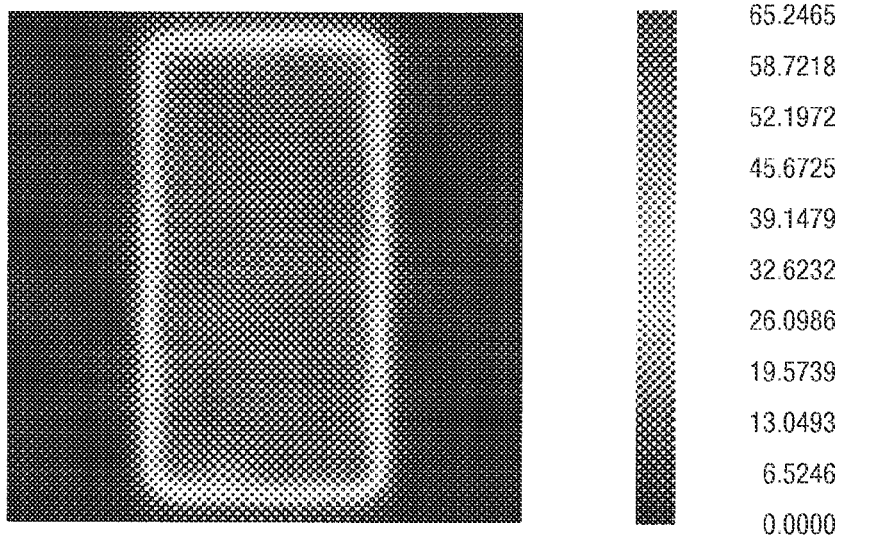

FIG. 40 and FIG. 41 show the irradiance at the input and output of the concentrator. Their comparison demonstrates the high efficiency (>98%) of light concentration provided by the input light pipe. Experimentally measured collection efficiency was a little lower: 95.6%.

FIG. 40 demonstrates highly non-uniform irradiance with highlighted peaks from 19 emitters of the laser bar. After homogenizing by concentrator, the irradiance distribution shown in FIG. 41 becomes almost flat.

Figure 42:
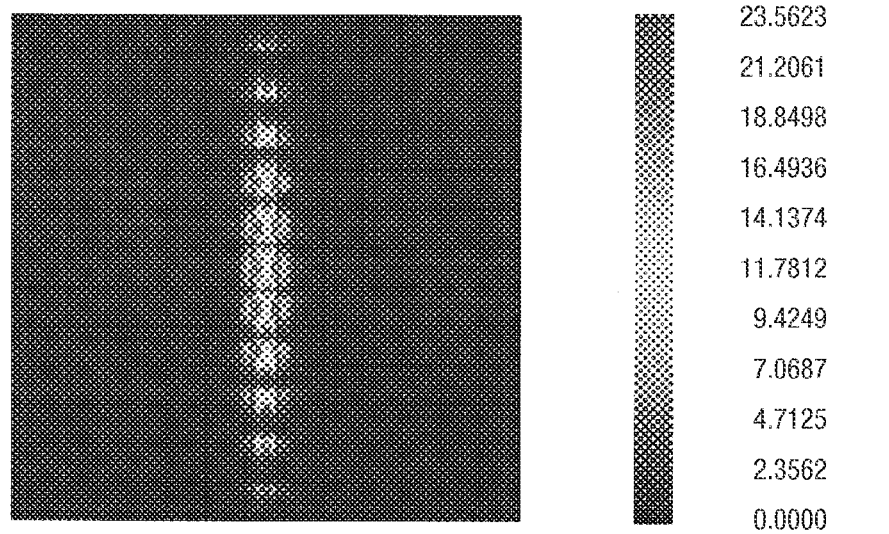
FIG. 42 demonstrates the radiant intensity of the light at the output of the concentrator.

FIG. 42 shows the dependence of the power delivered to the concentrator output on the tilt angle of rays to the axis. The displayed angles +/−42.3° correspond to the angular range accepted by the cytop fiber. As indicated by the amount of the power selected by these conditions, 96% of the input light can be accepted by fiber. The vertically arranged separate angular peaks are produced by virtual light sources, which are generated by sequential reflections from the side of concentrator, similar to the process described in FIG. 19.

Figure 43:
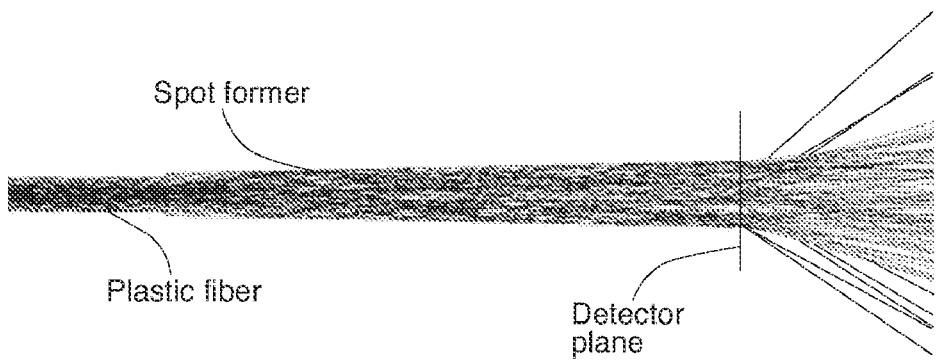
FIG. 43 shows the ray paths of the output beam and irradiance distribution at the exit of the spot former.
Figure 43:
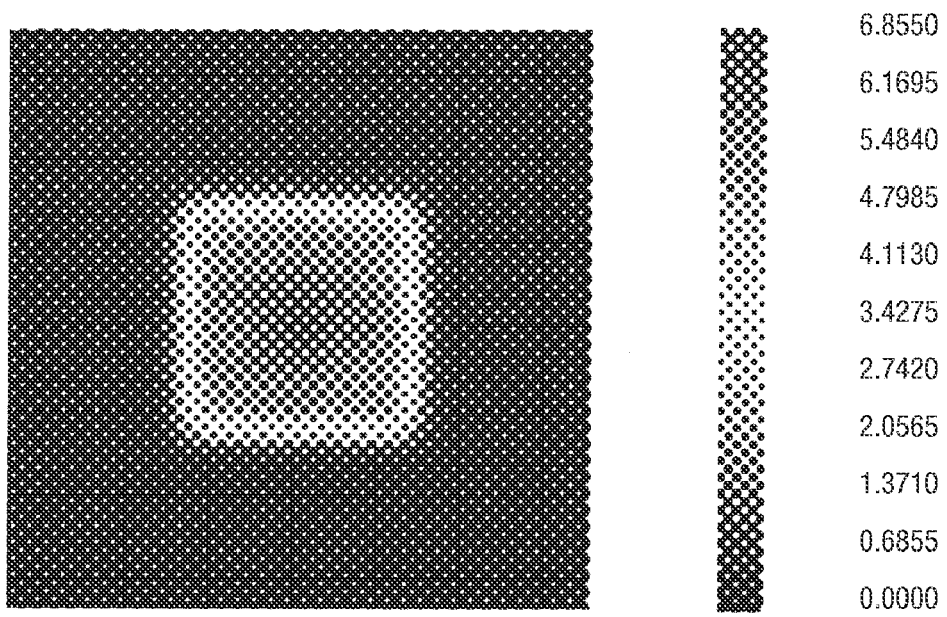
Figure 44:
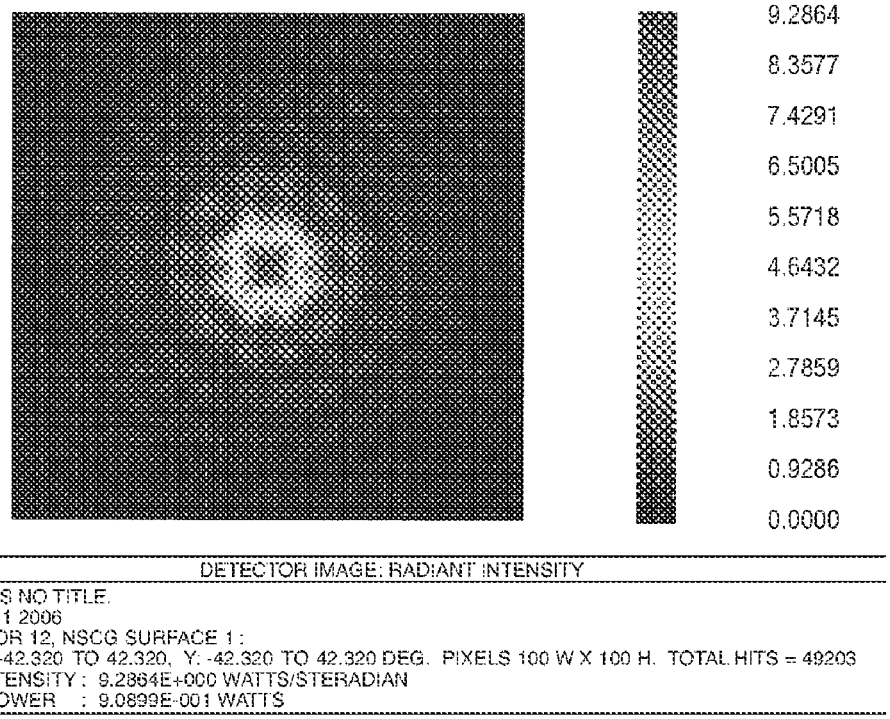
FIG. 44 illustrate the radiant intensity distribution at the spot former exit.

The ray traces and irradiance distribution at the system output are shown in FIG. 43. One can see that the spot former provides the output beam with uniform irradiance and with square shape. The total calculated efficiency of the light delivery is 91%. The divergence of the output beam is ~+/−8 degree, as can be seen from FIG. 44. The small amount of divergence keeps the spot shape and size almost unchanged for some distance from the output face.

As mentioned above, the collection efficiency of concentrator was measured experimentally and gave the amount of 95.6%. The dependence of this efficiency on the shift of concentrator related to laser bar was also determined experimentally.

Figure 45:
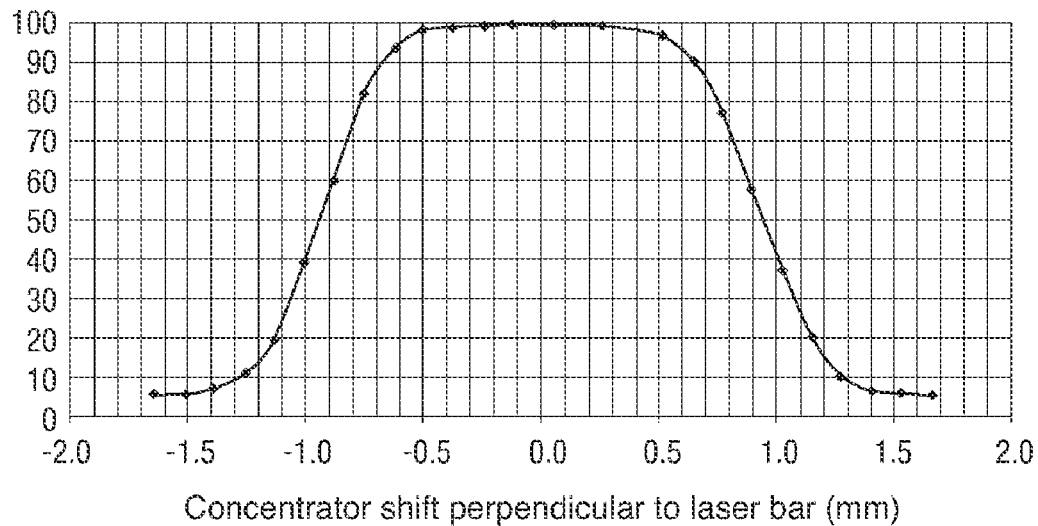
FIG. 45 demonstrates the results of measurements of collection efficiency of the concentrator.

FIG. 45 graphically represents the result of these measurements. As the transmitted power is not changed for the relative shifts +/−0.5 mm, the power of laser bar is substantially acquired by concentrator. The value of this non-sensitive shift determines the 1-mm tolerance for the relative position of bar and concentrator. So large tolerance value is very rare in optical alignment requirements, which usually belong to the range of some hundredths of millimeter.

Figure 46:
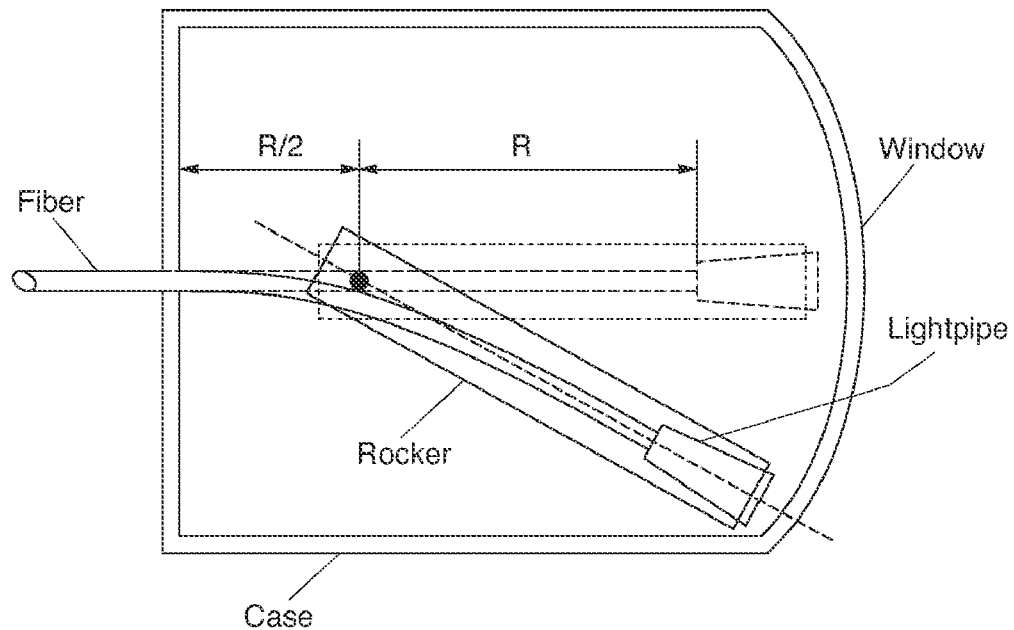
FIG. 46 is an illustrative view of a scanning device.

Monolithic nature of the described optical system eliminates the problem of relative alignment of its elements. Due to this property, the output beam can be easily scanned just by bending the fiber near the output light pipe (spot former). The scale of this deformation should be within the range, which avoids significant bending-related losses of the transmitted light. FIG. 46 shows the exemplary schematic diagram of scanning geometry according to the disclosed technology.

The scanning unit contains the rocker installed inside the case. The fiber is mounted to the rocker near the output light pipe, and is loosely held in the slit or hole made in the case wall. The gap between fiber and hole is made as small as possible. When rocker is periodically shifted from its original position, the fiber is bent, and the direction of output beam axis is changed providing beam scanning. The important issue is the position of rocker pivot point. Fiber is deformed as if it is cantilevered in the hole. In this case, the shape of the bent fiber is the cubic parabola having a tangent at the end, which always crosses the same point. The rocker rotational axis should coincide with this point. As shown in FIG. 46, the point is located on the original fiber direction at one third of total fiber length from the case wall. This position of pivot point provides the minimal shear deformation of fiber.

Figure 47:
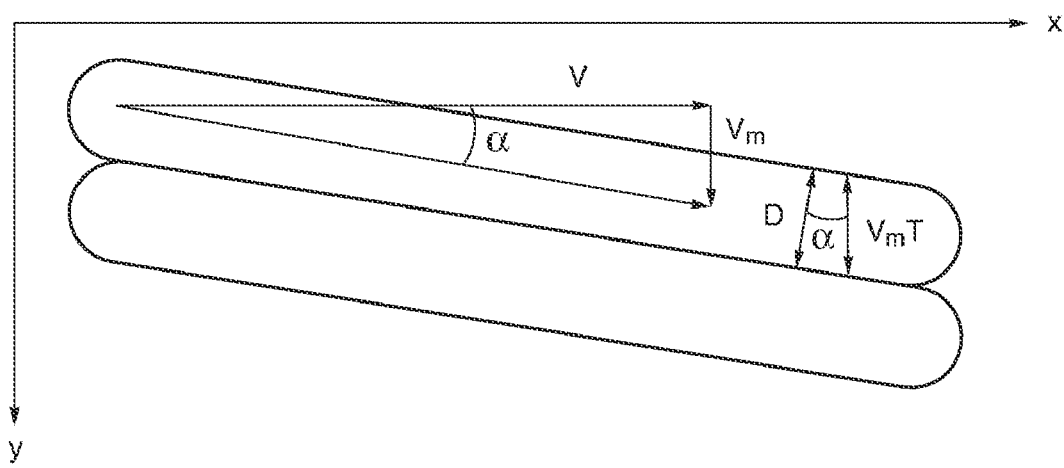
FIG. 47 is a diagram which depicts an area treated by a combination of scanning and manual movement of an embodiment of the device.

With each of the scanning embodiments described above, a strip of treated area at a desired depth is produced during each scan duration. The width of strip at the surface is equal to the spot diameter but increases with depth. As necessary, the same area may be treated over multiple passes to produce the desired degree of hair damage to modulate growth. The optimal manual speed should provide the shift of the strip by its width during the scan period. The scanning speed (V) is directed along the output window of the scanning head. The manual speed ($V_m$) is perpendicular to (V). From FIG. 47, it is seen that the scanning line is tilted to the direction of output window at angle determined by equation:

$$\tan \alpha = V_m/V \tag{36}$$

When the manual speed is optimal, the strip is shifted by its width (D) for the scanning period (T):

$$V_m^{opt} T \cos \alpha = D \tag{37}$$

Scanning length (L) can be expressed as:

$$L = VCT \tag{38}$$

where (C) is the useful fraction of scanning period, the duty cycle, of scanning. From the last three equations ($V_m$) is derived as:

$$V_m^{opt} = \frac{V}{\sqrt{\left(\frac{L}{CD}\right)^2 - 1}} \tag{39}$$

Substituting (V) from equation (5) into the last equation, the formula for the optimal amount of manual scanning speed is determined by:

$$V_m^{opt} = \frac{\frac{Kd}{\tau}}{\sqrt{\left(\frac{L}{CKd}\right)^2 - 1}} \tag{40}$$

The actual manual speed provided by operator is measured with movement sensor incorporated into the scanning head. The preferred design of this sensor is made similar to optical mouse and contains an illumination source such as an LED or diode laser, a detector, and a processor with an embedded algorithm for the speed calculation. When actual manual speed is higher than optimal one, the treatment area will contain untreated strips. If the scanning speed is not changed, this situation cannot be corrected by power adjustment and should be avoided. In one embodiment the device notifies the operator that manual speed must be reduced by generating a visual, audible or tactile warning signal.

Figure 48A:
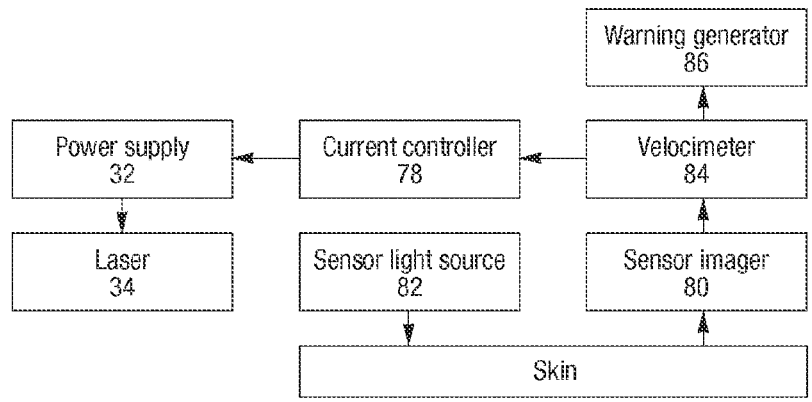
FIG. 48(a-c) are block diagrams of various embodiments of a treatment device with velocity sensing and adjustment of laser power.

Referring to FIG. 48a, a block diagram of a system is shown that can detect the motion of the head across the skin. In each embodiment the power supply 32 generates the working current for the laser 34. The power to the laser 34 is controlled by a controller 78. The treatment device contains the movement sensor such as is used in an optical computer mouse. The small area of skin, which is not currently under the laser treatment, is illuminated by a light source 82. An image of this area is detected by image detector 80. Preferably, the spectral range of light source 82 and spectral sensitivity of image detector 80 should be different than the wavelength of the treatment laser 34. Otherwise, the image detected by 80 is distorted by the scattered and reflected light from laser 34. A light-emitting diode (LED) or low-power laser diode (LD) is used as a light source 82. The image detector 80 is made as a small two-dimensional CCD or CMOS array. The size of the array is large enough to generate the image pattern of skin, which is specific for each position of sensor. The period between sequential images is set to be smaller than the shortest time required for illuminated area to shift by its size over the skin.

A velocimeter 84 measures the speed of manual movement using a pattern recognition algorithm and the image frame period. It also compares the measured velocity with given amount of optimal manual speed. If the measured speed is higher than the optimal speed, the warning generator 86 is activated or the power/scan rate is adjusted. The warning generator 86 is implemented as a blinking LED and/or a beeper to let the operator know that manual speed should be reduced. If the measured speed is lower than the optimal one, the velocimeter 84 provides the ratio of the measured to the optimal speed to the controller 78. The controller 78 varies the power to provide the change of laser output power according to the equation (42) or (46) as shown below.

Figure 49:
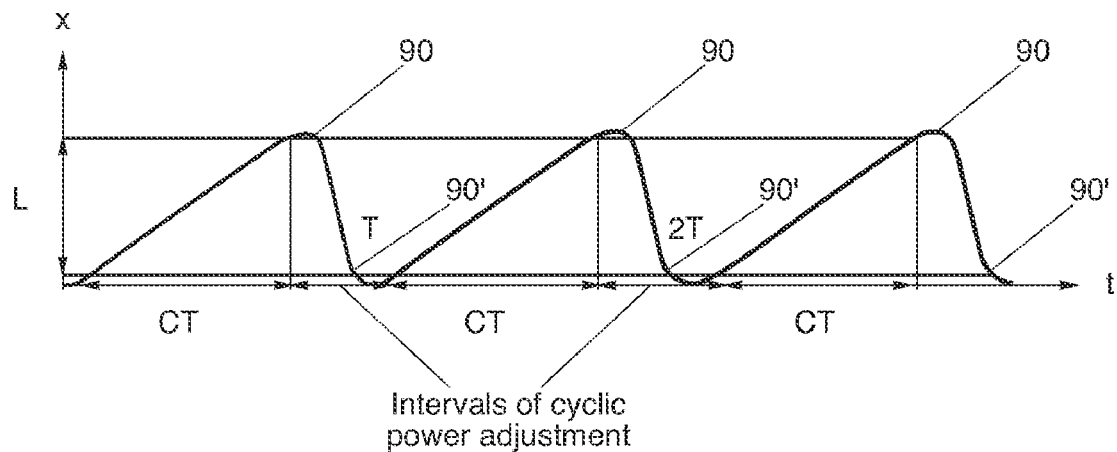
FIG. 49 is a graph showing the movement of the scanning spot with time as produced by the embodiments depicted in FIGS. 10, 12, 12a, 13.

For embodiments other than polygon-based one, additional power adjustment should be provided. In these cases, such as when the spot scanning achieved by an oscillating mirror movement as depicted in FIGS. 10 and 13. In these cases, the movement of the beam is shown generally in FIG. 49. The working range within the period (T) is limited by linear part of the curve when the spot displacement is uniformly increased with time. After the end of each working cycle, the spot is quickly returned to the initial position. This is necessary to provide for unidirectional beam scanning, which provides the continuous coverage of the treated area as shown in FIG. 49. The ratio of working range to the full period (T) gives the amount of duty cycle (C).

Near the turning points 90, 90' of the oscillation, the scanning speed of the spot is low. If the power delivered with spot is kept the same as during the fast phase of scanning, the skin at these points will be overheated. To avoid this, the power during the idle part of the period $(1-C)T$ is reduced or can be turned off. This type of power adjustment will be called "cyclic," as opposed to the "corrective" adjustment described above. Cyclic power adjustment is not needed for the polygon-based scanning system because the spot speed is not varied in this case.

Figure 48B:
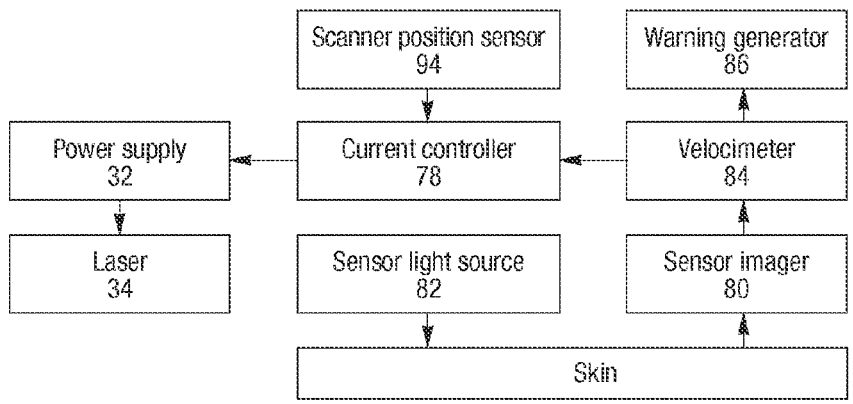

FIG. 48b shows the block diagram of the laser power adjustment for embodiments than polygon-based one. The current controller 78 is affected by signals from a scanner position sensor 94, in addition to those from velocimeter 84 as in FIG. 48a. Referring to the described above embodiments, the sensor measures the angular position of moving elements in designs of FIG. 10, or 13, or linear position of the fiber tip in design of FIG. 12. At the pre-determined positions, it gives the signals to controller for the reduction (or turning off) of the laser current and for its resuming.

In order to provide operator some range of manual speed, the movement with lower speed can be corrected by adjustment of laser power. In this case, each point of the treated area will receive multiple pulses of the same width. The number of pulses N is equal to the ratio between optimal and actual manual speed:

$$N = V_m^{opt}/V_m \qquad (41)$$

The power should be adjusted so that the total target modification after delivery of N pulses is the same as from the single pulse. The power decrease depends upon whether the device is used to produce photochemical effects or thermal effects.

For photochemical reactions, such as production of active oxygen forms during photodynamic therapy (PDT), the number of transformed molecules is directly proportional to the number of absorbed photons. Therefore, the power should be adjusted in reverse proportion to the pulse number N. That is, the power should be adjusted, in direct proportion to the actual manual speed:

$$P = P_{opt} V_m / V_m^{opt} \qquad (42)$$

The mechanism of photothermal reaction (selective photothermolysis) is more complicated. In this case, the light energy is used to heat the target and therefore accelerate the chemical reaction rate. As the target does not usually contain a light absorbing substance, the light first heats some distant object that contains high concentration of absorbing chromophore. The heat diffuses from the absorber to the surrounding tissues so the target temperature does not increase instantly with illumination but after the delay ($\tau_0$) called thermal relaxation time. The amount of ($\tau_0$) is proportional to the square of distance between absorber and target. The target selectivity is achieved by selection of light pulse duration ($\tau$) approximately equal to ($\tau_0$). If ($\tau < \tau_0$), the target temperature is not increased enough to accelerate the chemical reaction. At the terminal end of light pulse, only the regions that are closer to the absorber are heated. If ($\tau > \tau_0$), the heat diffuses too far from the absorber and may cause chemical modifications in surrounding tissues, not only in target. For the permanent hair removal, the hair shaft containing the highly absorptive chromophore, melanin, serves as an absorber, and hair bulb is considered target. The commonly used pulse width of 30 msec is roughly equal to the thermal relaxation time of hair bulb. In addition to the pulse width, the peak power should be also selected to provide enough target heating.

For thermally activated reactions, the reaction rate k is determined by Arrhenius law:

$$k = A \mathrm{Exp}(-\Delta E/RT) \qquad (43)$$

where ($\Delta E$) is reaction activation energy, (A) is reaction rate at infinite temperature, and (RT) is thermal energy proportional to absolute temperature (T). Considering the number of transformed molecules the same for single and (N) pulses of the same duration, the connection between temperature ($T_1$) under optimal power and ($T_2$) under reduced power should be the following:

$$\mathrm{Exp}(-\Delta E/RT_1) = N\mathrm{Exp}(-\Delta E/RT_2) \qquad (44)$$

The heating of the target is proportional to the laser power, because pulse duration is kept the same:

$$(T_1-T_0)/(T_2-T_0)=P_{opt}/P \quad (45)$$

Here $T_0=310$ K is human body temperature. From the last two equations, one can receive the equation for the power adjustment:

$$P = P_{opt}\frac{T_0}{T_1-T_0}\left[\frac{\frac{T_1}{T_0}}{1-\frac{RT_1}{\Delta E}\ln\left(\frac{V_m}{V_m^{opt}}\right)} - 1\right] \quad (46)$$

Adjusted power in equation (46) depends logarithmically on $V_m$, which is not as strong as the dependence on $V_m$ as given by equation (42). Therefore, only minor power adjustment is expected for thermally activated reactions.

Figure 50:
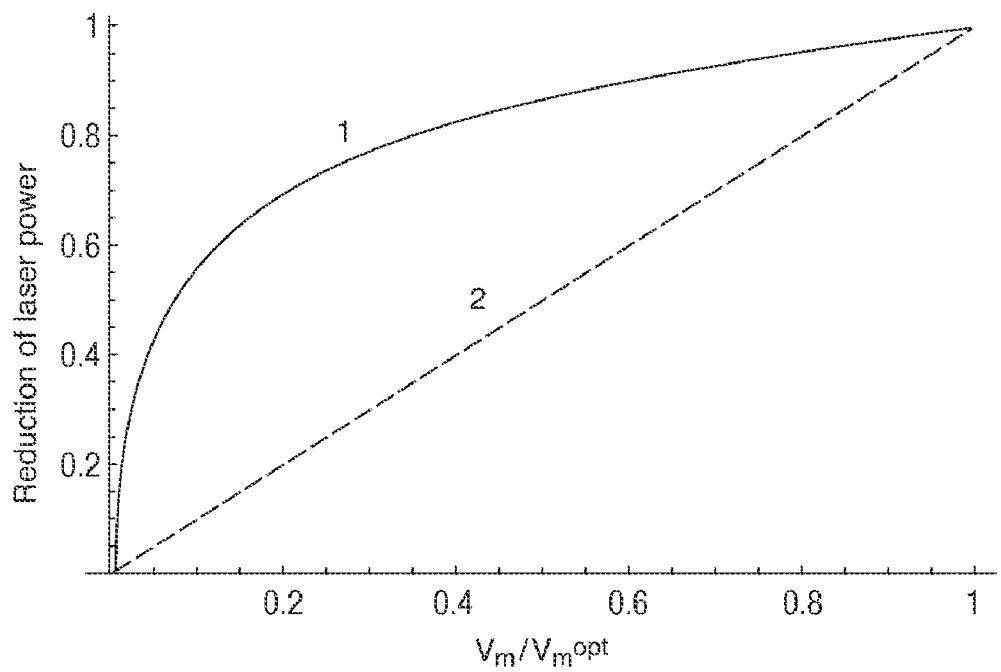
FIG. 50 is a graph of the reduction in laser power possible as the speed of use differs from the optimal speed.

FIG. 50 shows the decrease in power that can be used when the speed deviates from the optimal speed. The graph 1 refers to photothermal reaction and is based on equation (46). The values of the equation parameters used are reported in the literature: $\Delta E=327$ kJ/mol for bulk skin damage, and $T_1=50°$ C. as a threshold temperature for reduction of enzyme activity. The graph 2 corresponds to photochemical reactions, in accordance to equation (42).

Referring again to FIGS. 48a and 48b, the current controller 78 provides the corrective power adjustment according to the equations (42) or (46) based on the signals from velocimeter 84. The set of input parameters: $V_m^{opt}$, selection between equations (42) and (46), $\Delta E$, and $T_1$ can be entered by the operator using a key digit pad separately or can be switched between the sets, which are generated for different tasks and saved in the device memory.

A more advanced way of corrective power adjustment can be achieved with simultaneous adjustment of scanning speed. Referring to equation (39) and FIG. 47, when scanning speed V varies in direct proportion to changing $V_m$ the treatment strips do not overlap each other and optimal treatment conditions are kept. In this case, there are no multiple pulses received by target but pulse duration is changed in the reversed proportion to the scanning speed. Under this condition, the photothermolysis produces the same amount of transformed molecules if the total delivered fluence is kept approximately constant. That means the power adjustment with simultaneous correction of scanning speed is described by equation (42) for both photothermal and photochemical reactions. But adjustment range for photothermolysis is limited at both extremes. Too low manual and scanning speeds should be avoided because the amount of pulse width ($\tau$) (see equation (5)) may become much more than thermal relaxation time ($\tau_0$) that is far from optimal conditions. Too high a manual speed would require according to equation (42) the output power higher than maximal value provided by the used laser. The operator is warned about using an out-of-range manual speed to avoid these conditions.

Figure 48C:
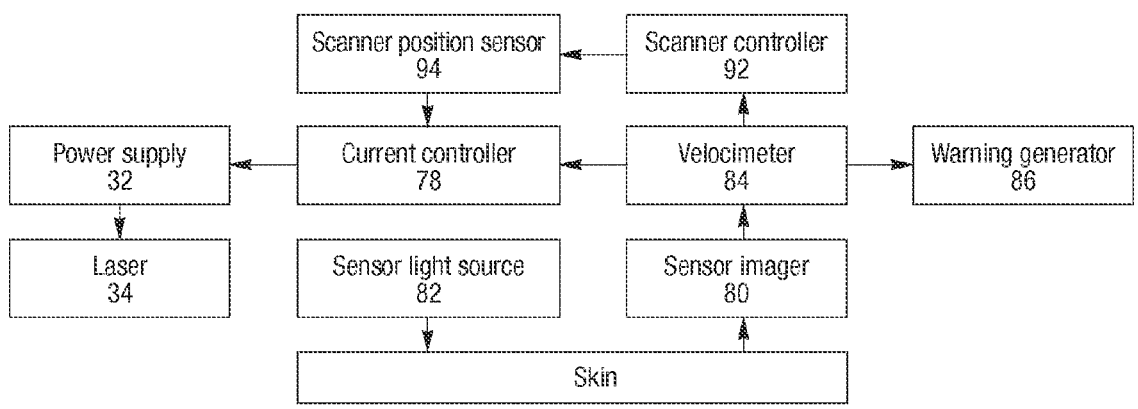

FIG. 48c shows the block diagram of the device with adjustment of both laser power and scanning speed. Velocimeter 84 affects current controller 78 in two ways. The first is the same as in FIGS. 48a and 48b: the current is corrected to provide the satisfaction of equation (42) based on the data about the measured manual speed. In addition to corrective adjustment, the velocimeter 84 affects cyclic adjustment through a scanner controller 98, which varies the scanning speed in direct proportion to the manual one, and scanner position sensor 94. Again, the warning generator 86 is activated when manual speed is either too low or too high.

Occasionally the operator will manually pass the same area multiple times. This will not result in any problem with overdosing the treatment area but at the same time, there will be no added advantage compared to a single pass. The treatment effect from multiple pulses is considered above and described by equation (43), where the ratio $V_m^{opt}/V_m$ should be replaced with number of passes (N). One can see from FIG. 50 (curve 1) that the laser power can be kept almost the same until $N<10(V_m/V_m^{opt}>0.1)$.

As multiple passes do not bring significant advantages but extend the treatment time, they preferably should be avoided. To provide this, some clearly visible substance can be applied to the part of the skin surface to be treated. Such substance can be for example foam similar to shaving cream, or colorized indicator liquid. The mentioned substance should not strongly absorb the treatment light. In this case, the scanning head is equipped with the surface cleaning means such as a plate with a blunt edge positioned perpendicular to the skin surface in front of output window. The length of this plate is equal to the length of the scanning line of the laser spot. During the manual movement of the scanning head, the cleaning means removes the covering substance from the treated part of the skin surface allowing operator to distinguish the treated from untreated parts. In one embodiment, the cleaning means does not remove the covering substance completely, but leaves a thin film on the surface. The residual film serves as a lubricant for the manual movement of scanning head on skin.

Although the specific embodiments described above are based on lasers, the non-coherent intense pulse light (IPL) sources can be used. The short pulse of IPL is typically provided by the discharge of a condenser battery having high capacitance. The battery is charged between pulses. The generated light is spectrally filtered in the desired wavelength range, and focused with reflective and refractive optics on the output window within a small spot. The following behavior of IPL light inside the skin does not differ from the diffusion of laser light, and can be used in all described embodiments. The only difference is the stepwise scanning manner of IPL spot because of pulse mode.

Although the disclosed technology has been described in terms of hair removal, the disclosed technology can be used to treat other dermatological problems. Scanned small spot lasers that penetrate up to 3 mm into the skin have the potential to improve a variety of skin conditions such as vascular lesions, pigmented lesions and a variety of other conditions including photoaged skin and wrinkling. In the treatment of vascular lesions, absorption in hemoglobin with conversion of light to heat energy damages the endothelial lining and causes damage to papillary dermal vessels. The result is an improvement in facial telangiectasia, diffuse facial redness, facial flushing, as well as in the treatment of spider veins of the face and legs. Port wine stains and hemangiomas also respond to treatment with these devices. As long as the scanned time of the continuous wave scan spot is on the order of microseconds to milliseconds, sufficient thermal injury will be achieved to obtain improvement in this group of vascular lesions.

Pigmented lesions also respond to the scanned small spot devices. Lentigines, sun induced epidermal pigmented lesions and other epidermal pigmented lesions that are present at birth or delayed birth marks such as cafe au lait macules, Becker's nevus, nevus spillus also respond. Melasma and post-inflammatory hyperpigmentation, which are either combined epidermal and dermal pigmented disorders or solely dermal pigmented disorders, also respond to treatment by interrupting the dermal pigmentary process.

Photoaging presents as coarseness, roughness and sallowness of skin of skin as well as other changes including telangiectasia, dyspigmentation. All can be improved with the scanned small spot laser and light sources. Research has proven that a variety of different wavelengths from the short visible to the mid-infrared range stimulate new collagen production in the papillary and mid-dermis. The absorbing chromophore that initiates this change has not yet been determined. It appears, however, that a variety of different skin chromophores, including water, melanin pigment, and hemoglobin all can serve as the chromophore that absorbs the light to initiate this effect. Light energy converts to heat energy and by some yet to be determined biologic and cellular event, stimulates fibroblasts to produce new collagen. Studies have shown that a variety of these wavelengths can induce production of new type I and type III collagen fibers. Scanned small spot lasers and light sources also stimulate fibroblasts to produce collagen and induce, in effect, frequently terms "photorejuvenation." This change which is hardest to show photographically is easy to measure using profilometric measurement and also on skin biopsy. These biopsies show a Grenz zone of new collagen in the papillary dermis replacing the photo damaged collagen, and this accounts for the improvement in coarseness of skin, roughness of skin, skin texture. Absorption of light in vasculature and in pigmented areas accounts for the improvement of skin color, both red and brown, and for the total photorejuvenation effect.

Although the disclosed technology has been described in terms of using light as the energy source, it is anticipated that the energy source could also include microwaves, ultrasound and other directed sources when used with the proper system to provide narrow beam energy to the desired treatment depth without damaging tissues not meant for treatment.

The mechanism of microwave influence is based on the induction of electrical current in media, which is finally converted into heat. Therefore, the previous consideration about thermally activated chemical reactions can be applied to this case.

Ultrasound is often employed for its tissue heating functionality. However, the phenomena of resonant absorption, such as used in ultrasound lithotripsy applications, can also be integrated in the embodiments disclosed herein. If an object, such as a kidney stone, has a size that approaches the ultrasound wavelength, energy absorption can be strong enough such that the object is destroyed by resonant waves. To produce the desirable resonance, the object should respond to ultrasound, while the surrounding media, i.e. tissue, should remain unresponsive and undamaged. As the chemical structure and mechanical properties of hair are quite different from surrounding soft tissues of the body, it is reasonable to expect the resonant interaction between hair shaft and ultrasound to allow hair removal without tissue damage. Because of the resonant nature of the interaction, this embodiment requires less power than other direct thermal applications.

What is claimed is:

1. An optical system for temporarily affecting hair growth on a patient's skin, the optical system comprising: a laser bar adapted to produce light energy appropriate for affecting hair growth on a patient's skin; a light pipe optically coupled to the laser bar and adapted to convey at least some of the light energy to a first target region on the patient's skin; and a scanning mechanism mechanically coupled to the light pipe, the scanning mechanism including a shaft with two helical grooves to facilitate changing an orientation of the light pipe so that the conveyed light energy is directed at a second target region on the patient's skin.

2. The optical system of claim 1, wherein the light pipe and scanning mechanism are contained within an optical head.

3. The optical system of claim 2, wherein the light pipe is tapered having an input face of about 10 mm by 3 mm and an output face of about 4 mm by 4 mm.

4. The optical system of claim 2, wherein the light pipe is adapted to convey at least 95% of the light energy produced by the laser bar to the first target region.

5. The optical system of claim 4, wherein the light pipe is tapered having an input face of about 10 mm by 3 mm and an output face of about 4 mm by 4 mm.

6. The optical system of claim 1, wherein the light pipe is adapted to convey at least 95% of the light energy produced by the laser bar to the first target region.

7. The optical system of claim 1, wherein the light pipe is tapered having an input face of about 10 mm by 3 mm and an output face of about 4 mm by 4 mm.

8. The optical system of claim 1, wherein the laser bar is spaced about 1 mm from the light pipe.

9. The optical system of claim 1, wherein the change in orientation of the light pipe exhibits an angular magnitude of about 7 degrees.

10. The optical system of claim 1, wherein the length of the light pipe is selected to minimize divergence of the light energy conveyed to the first target region.

* * * * *